US011259920B2

(12) United States Patent
Luong et al.

(10) Patent No.: US 11,259,920 B2
(45) Date of Patent: Mar. 1, 2022

(54) ADAPTER FOR PROSTHESIS DELIVERY DEVICE AND METHODS OF USE

(71) Applicant: Edwards Lifesciences Corporation, Irvine, CA (US)

(72) Inventors: Hieu Minh Luong, Westminster, CA (US); Garrett Dallas Johnson, Costa Mesa, CA (US); Juan Valencia, Santa Ana, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 722 days.

(21) Appl. No.: 15/298,055

(22) Filed: Oct. 19, 2016

(65) Prior Publication Data

US 2017/0119526 A1 May 4, 2017

Related U.S. Application Data

(60) Provisional application No. 62/383,132, filed on Sep. 2, 2016, provisional application No. 62/250,359, filed on Nov. 3, 2015.

(51) Int. Cl.
*A61F 2/24* (2006.01)
*A61B 90/57* (2016.01)
*A61B 90/11* (2016.01)
*A61F 2/95* (2013.01)

(52) U.S. Cl.
CPC ............ *A61F 2/2427* (2013.01); *A61B 90/11* (2016.02); *A61B 90/57* (2016.02); *A61F 2/9517* (2020.05)

(58) Field of Classification Search
CPC ........... A61F 2/2427; A61F 2002/9517; A61B 90/11; A61B 90/57; A61B 90/50; A61G 13/101; B25B 5/006

USPC ......... 248/279.1, 287.1, 286.1, 298.1, 276.1, 248/274.1; 403/57, 58, 81
See application file for complete search history.

(56) References Cited

U.S. PATENT DOCUMENTS

| | | | | |
|---|---|---|---|---|
| 2,681,058 A | * | 6/1954 | Mathues | A61B 17/6433 602/17 |
| 4,001,556 A | * | 1/1977 | Folchi | B25J 13/081 414/5 |
| 4,035,849 A | | 7/1977 | Angell et al. | |
| 4,132,318 A | * | 1/1979 | Wang | B25J 13/082 294/86.4 |

(Continued)

FOREIGN PATENT DOCUMENTS

| | | |
|---|---|---|
| DE | 19532846 A1 | 3/1997 |
| DE | 19907646 A1 | 8/2000 |

(Continued)

OTHER PUBLICATIONS

Int'l. Search Report for PCT/US2016/057976, dated Nov. 15, 2017.

(Continued)

*Primary Examiner* — Joel D Crandall
(74) *Attorney, Agent, or Firm* — Knobbe Martens Olson & Bear LLP

(57) ABSTRACT

Disclosed herein are embodiments of adapters that can be used to translate and/or rotate the position of a delivery system, such as for use with a replacement mitral valve. The adapters can allow for three-dimensional motion of the delivery system, thus allow for precise positioning and movement of the delivery system during use by an operator.

18 Claims, 16 Drawing Sheets

(56) References Cited

U.S. PATENT DOCUMENTS

| | | | |
|---|---|---|---|
| 4,317,560 A * | 3/1982 | Troyer | B23K 37/0452 266/48 |
| 4,365,488 A * | 12/1982 | Mochida | F16D 3/38 403/57 |
| 4,592,340 A | 6/1986 | Boyles | |
| 4,596,509 A * | 6/1986 | Ise | B23Q 1/28 414/749.4 |
| 4,686,997 A * | 8/1987 | Oloff | A61B 10/025 600/436 |
| 4,955,895 A | 9/1990 | Sugiyama et al. | |
| 4,994,077 A | 2/1991 | Dobben | |
| 5,059,177 A | 10/1991 | Towne et al. | |
| 5,062,730 A * | 11/1991 | Tomii | F16D 3/38 403/57 |
| 5,176,652 A | 1/1993 | Littrell | |
| 5,176,698 A | 1/1993 | Burns et al. | |
| 5,184,601 A * | 2/1993 | Putman | B25J 9/042 312/209 |
| 5,304,198 A | 4/1994 | Samson | |
| 5,332,402 A | 7/1994 | Teitelbaum | |
| 5,358,496 A | 10/1994 | Ortiz et al. | |
| 5,411,552 A | 5/1995 | Andersen et al. | |
| 5,554,185 A | 9/1996 | Block et al. | |
| 5,571,072 A | 11/1996 | Kronner | |
| 5,591,195 A | 1/1997 | Taheri et al. | |
| 5,599,305 A | 2/1997 | Hermann et al. | |
| 5,626,595 A * | 5/1997 | Sklar | A61B 17/320016 606/170 |
| 5,632,760 A | 5/1997 | Sheiban et al. | |
| 5,639,274 A | 6/1997 | Fischell et al. | |
| 5,728,068 A | 3/1998 | Leone et al. | |
| 5,776,099 A | 7/1998 | Tremulis | |
| 5,840,081 A | 11/1998 | Andersen et al. | |
| 5,855,583 A * | 1/1999 | Wang | A61B 17/11 318/568.11 |
| 5,876,325 A * | 3/1999 | Mizuno | A61B 1/00048 600/102 |
| 5,908,405 A | 6/1999 | Imran et al. | |
| 5,968,068 A | 10/1999 | Dehdashtian et al. | |
| 5,968,069 A | 10/1999 | Dusbabek et al. | |
| 6,027,510 A | 2/2000 | Alt | |
| 6,033,381 A | 3/2000 | Kontos | |
| 6,146,339 A | 11/2000 | Biagtan et al. | |
| 6,168,614 B1 | 1/2001 | Andersen et al. | |
| 6,217,585 B1 | 4/2001 | Houser et al. | |
| 6,235,050 B1 | 5/2001 | Quiachon et al. | |
| 6,264,683 B1 | 7/2001 | Stack et al. | |
| 6,379,372 B1 | 4/2002 | Dehdashtian et al. | |
| 6,454,799 B1 | 9/2002 | Schreck | |
| 6,458,153 B1 | 10/2002 | Bailey et al. | |
| 6,461,382 B1 | 10/2002 | Cao | |
| 6,514,228 B1 | 2/2003 | Hamilton et al. | |
| 6,527,979 B2 | 3/2003 | Constantz | |
| 6,540,782 B1 | 4/2003 | Snyders | |
| 6,579,305 B1 | 6/2003 | Lashinski | |
| 6,652,578 B2 | 11/2003 | Bailey et al. | |
| 6,730,118 B2 | 5/2004 | Spenser et al. | |
| 6,733,525 B2 | 5/2004 | Yang et al. | |
| 6,746,471 B2 | 6/2004 | Mortier et al. | |
| 6,764,504 B2 | 7/2004 | Wang et al. | |
| 6,767,362 B2 | 7/2004 | Schreck | |
| 6,830,584 B1 | 12/2004 | Seguin | |
| 6,893,460 B2 | 5/2005 | Spenser et al. | |
| 6,908,481 B2 | 6/2005 | Cribier | |
| 7,018,406 B2 | 3/2006 | Seguin et al. | |
| 7,018,408 B2 | 3/2006 | Bailey et al. | |
| 7,276,084 B2 | 10/2007 | Yang et al. | |
| 7,318,278 B2 | 1/2008 | Zhang et al. | |
| 7,374,571 B2 | 5/2008 | Pease et al. | |
| 7,381,219 B2 | 6/2008 | Salahieh et al. | |
| 7,393,360 B2 | 7/2008 | Spenser et al. | |
| 7,510,575 B2 | 3/2009 | Spenser et al. | |
| 7,585,321 B2 | 9/2009 | Cribier | |
| 7,594,926 B2 | 9/2009 | Linder et al. | |
| 7,597,709 B2 | 10/2009 | Goodin | |
| 7,618,446 B2 | 11/2009 | Andersen et al. | |
| 7,621,948 B2 | 11/2009 | Herrmann et al. | |
| 7,785,366 B2 | 8/2010 | Maurer et al. | |
| 7,950,306 B2 * | 5/2011 | Stuart | B25J 9/106 74/490.01 |
| 8,029,556 B2 | 10/2011 | Rowe | |
| 8,052,750 B2 | 11/2011 | Tuval et al. | |
| 8,167,932 B2 | 5/2012 | Bourang | |
| 8,182,530 B2 | 5/2012 | Huber | |
| RE43,882 E | 12/2012 | Hopkins et al. | |
| 8,407,380 B2 | 3/2013 | Matsunaga et al. | |
| 8,449,606 B2 | 5/2013 | Eliasen et al. | |
| 8,568,472 B2 | 10/2013 | Marchand et al. | |
| 8,747,460 B2 | 6/2014 | Tuval et al. | |
| 8,771,345 B2 | 7/2014 | Tuval et al. | |
| 8,771,346 B2 | 7/2014 | Tuval et al. | |
| 8,834,564 B2 | 9/2014 | Tuval et al. | |
| 8,876,894 B2 | 11/2014 | Tuval et al. | |
| 8,876,895 B2 | 11/2014 | Tuval et al. | |
| 9,078,749 B2 | 7/2015 | Lutter et al. | |
| 9,138,312 B2 | 9/2015 | Tuval et al. | |
| 9,163,893 B1 * | 10/2015 | Gutierrez | F41A 23/16 |
| 2002/0032481 A1 | 3/2002 | Gabbay | |
| 2003/0050694 A1 | 3/2003 | Yang et al. | |
| 2003/0081953 A1 | 5/2003 | Wei | |
| 2003/0114913 A1 | 6/2003 | Spenser et al. | |
| 2003/0130571 A1 | 7/2003 | Lattouf | |
| 2003/0158597 A1 | 8/2003 | Quiachon et al. | |
| 2003/0199975 A1 | 10/2003 | Gabbay | |
| 2004/0093060 A1 | 5/2004 | Seguin et al. | |
| 2004/0098081 A1 | 5/2004 | Landreville et al. | |
| 2004/0102791 A1 | 5/2004 | Murray | |
| 2004/0133263 A1 | 7/2004 | Dusbabek et al. | |
| 2004/0153135 A1 | 8/2004 | Haase et al. | |
| 2004/0186563 A1 | 9/2004 | Lobbi | |
| 2004/0186565 A1 | 9/2004 | Schreck | |
| 2004/0210304 A1 | 10/2004 | Seguin et al. | |
| 2004/0260389 A1 | 12/2004 | Case et al. | |
| 2005/0096736 A1 | 5/2005 | Osse et al. | |
| 2005/0137686 A1 | 6/2005 | Salahieh et al. | |
| 2005/0137687 A1 | 6/2005 | Salahieh et al. | |
| 2005/0137691 A1 | 6/2005 | Salahieh et al. | |
| 2005/0203614 A1 | 9/2005 | Forster et al. | |
| 2005/0203617 A1 | 9/2005 | Forster et al. | |
| 2005/0234435 A1 * | 10/2005 | Layer | A61B 17/3403 606/1 |
| 2005/0240200 A1 | 10/2005 | Bergheim | |
| 2005/0245894 A1 | 11/2005 | Zadno-Azizi | |
| 2006/0025857 A1 | 2/2006 | Bergheim et al. | |
| 2006/0229719 A1 | 10/2006 | Marquez et al. | |
| 2006/0282150 A1 | 12/2006 | Olson et al. | |
| 2007/0005131 A1 | 1/2007 | Taylor | |
| 2007/0027534 A1 | 2/2007 | Bergheim et al. | |
| 2007/0055289 A1 * | 3/2007 | Scouten | A61B 90/14 606/130 |
| 2007/0088431 A1 | 4/2007 | Bourang et al. | |
| 2007/0112422 A1 | 5/2007 | Dehdashtian | |
| 2007/0203575 A1 | 8/2007 | Forster et al. | |
| 2007/0265700 A1 | 11/2007 | Eliasen et al. | |
| 2007/0270943 A1 | 11/2007 | Solem et al. | |
| 2007/0270944 A1 | 11/2007 | Bergheim et al. | |
| 2008/0071366 A1 | 3/2008 | Tuval et al. | |
| 2008/0119922 A1 | 5/2008 | Alkhatib | |
| 2008/0125853 A1 | 5/2008 | Bailey et al. | |
| 2008/0226283 A1 * | 9/2008 | Yu | F16M 11/10 396/428 |
| 2008/0294230 A1 | 11/2008 | Parker | |
| 2009/0124428 A1 | 5/2009 | Sullivan et al. | |
| 2009/0138079 A1 | 5/2009 | Tuval et al. | |
| 2009/0157175 A1 | 6/2009 | Benichou | |
| 2009/0192585 A1 | 7/2009 | Bloom et al. | |
| 2009/0234428 A1 | 9/2009 | Snow et al. | |
| 2009/0276040 A1 | 11/2009 | Rowe et al. | |
| 2009/0281619 A1 | 11/2009 | Le et al. | |
| 2009/0299456 A1 | 12/2009 | Melsheimer | |
| 2009/0319037 A1 | 12/2009 | Rowe et al. | |
| 2010/0030318 A1 | 2/2010 | Berra | |
| 2010/0036472 A1 | 2/2010 | Papp | |

(56) References Cited

U.S. PATENT DOCUMENTS

| | | |
|---|---|---|
| 2010/0036473 A1 | 2/2010 | Roth |
| 2010/0049313 A1 | 2/2010 | Alon et al. |
| 2010/0076402 A1 | 3/2010 | Mazzone et al. |
| 2010/0076541 A1 | 3/2010 | Kumoyama |
| 2010/0082089 A1 | 4/2010 | Quadri et al. |
| 2010/0094394 A1 | 4/2010 | Beach et al. |
| 2010/0121425 A1 | 5/2010 | Shimada |
| 2010/0145431 A1 | 6/2010 | Wu et al. |
| 2010/0174363 A1 | 7/2010 | Castro |
| 2010/0198347 A1 | 8/2010 | Zakay et al. |
| 2010/0274344 A1 | 10/2010 | Dusbabek et al. |
| 2011/0001022 A1 | 1/2011 | Edinger |
| 2011/0004296 A1 | 1/2011 | Lutter et al. |
| 2011/0015729 A1 | 1/2011 | Jimenez et al. |
| 2011/0054596 A1 | 3/2011 | Taylor |
| 2011/0160846 A1 | 6/2011 | Bishop et al. |
| 2012/0069965 A1 | 3/2012 | Scheffer et al. |
| 2012/0123529 A1 | 5/2012 | Levi et al. |
| 2013/0073035 A1 | 3/2013 | Tuval et al. |
| 2013/0218266 A1 | 8/2013 | Chalekian et al. |
| 2013/0317598 A1 | 11/2013 | Rowe et al. |
| 2014/0379077 A1 | 12/2014 | Tuval et al. |
| 2015/0025549 A1 | 1/2015 | Kilroy et al. |
| 2015/0133958 A1* | 5/2015 | Singh ............... A61B 90/10 606/130 |

FOREIGN PATENT DOCUMENTS

| | | |
|---|---|---|
| DE | 102013002813 A1 | 8/2014 |
| EP | 0592410 A1 | 4/1994 |
| EP | 0850607 A1 | 7/1998 |
| EP | 1796597 A2 | 6/2007 |
| FR | 2815844 A1 | 5/2002 |
| KR | 10-0977615 B1 | 8/2010 |
| WO | 91/17720 A1 | 11/1991 |
| WO | 9829057 A1 | 7/1998 |
| WO | 0060995 A2 | 10/2000 |
| WO | 0149213 A2 | 7/2001 |
| WO | 0154625 A1 | 8/2001 |
| WO | 0176510 A2 | 10/2001 |
| WO | 0222054 A1 | 3/2002 |
| WO | 0236048 A1 | 5/2002 |
| WO | 0247575 A2 | 6/2002 |
| WO | 03047468 A1 | 6/2003 |
| WO | 03082121 A2 | 10/2003 |
| WO | 2005084595 A1 | 9/2005 |
| WO | 2005102015 A2 | 11/2005 |
| WO | 2006111391 A1 | 10/2006 |
| WO | 2006138173 A2 | 12/2006 |
| WO | 2007047488 A2 | 4/2007 |
| WO | 2007067942 A1 | 6/2007 |
| WO | 2009033469 A1 | 3/2009 |
| WO | 2010121076 A2 | 10/2010 |
| WO | 2012044869 A2 | 4/2012 |

OTHER PUBLICATIONS

M.D. Dake, et al., "Transluminal Placement of Endovascular Stent-Grafts for the Treatment of Descending Thoracic Aortic Aneurysms," The New England Journal of Medicine. vol. 331, No. 26. 1994. pp. 1729-1734.

Fanning, Jonathon P., et al., "Transcatheter Aortic Valve Implantation (TAVI): Valve Design and Evolution," International Journal of Cardiology 168 (2013) 1822-1831, Applicant believes this may have been available as early as Oct. 3, 2013.

Leon, Martin B., et al., "Transcatheter Aortic Valve Replacement in Patients with Critical Aortic Stenosis: Rationale, Device Descriptions, Early Clinical Experiences, and Perspectives," Semin. Thorac. Cardiovasc. Surg. 18:165-174, 2006 in 10 pages, Applicant believes this may have been available as early as the Summer of 2006.

Lutter, Georg, et al., "Off-Pump Transapical Mitral Valve Replacement," European Journal of Cardio-thoracic Surgery 36 (2009) 124-128, Applicant believes this may have been available as early as Apr. 25, 2009.

Treede et al.: "Transapical transcatheter aortic valve implantation using the JenaValve™ system: acute and 30-day results of the multicentre CE-mark study." http://ejcts.oxfordjournals.org/content/41/6/e131.long. Apr. 16, 2012.

Preston-Maher, Georgia L., et al., "A Technical Review of Minimally Invasive Mitral Valve Replacements," Cardiovascular Engineering and Technology, vol. 6, No. 2, Jun. 2015, pp. 174-184. Applicant believes this may have been available as early as Nov. 25, 2014.

Huber, Christoph H., et al. "Direct-Access Valve Replacement: A Novel Approach for Off-Pump Valve Implantation Using Valved Stents." J Am Coll Cardiol, 46(2):366-370, 369 (2005).

Andersen, Henning R., et al. "Transluminal Implantation of Artificial Heart Valves. Description of a New Expandable Aortic Valve and Initial Results with Implantation by Catheter Technique in Closed Chest Pigs." Eur Heart J, 13:704-708 (1992) ("Andersen").

Bonhoeffer, Philipp, et al. "Percutaneous Replacement of Pulmonary Valve in a Right-Ventricle to Pulmonary-Artery Prosthetic Conduit with Valve Dysfunction." Lancet, 356:1403-1405 (2000).

Cribier, Alain, et al. "Percutaneous Transcatheter Implantation of an Aortic Valve Prosthesis for Calcific Aortic Stenosis." Circulation, 106:3006-3008 (2002) ("Cribier").

Zhou, Jun Qing, et al. "Self-Expandable Valved Stent of Large Size: Off-Bypass Implantation in Pulmonary Position." Eur J Cardio-Thorac Surg, 24:212-216 (2003) ("Zhou").

Golding, Leonard, A. R. "New Cannulation Technique for the Severely Calcified Ascending Aorta." J Thorac Cardiovasc Surg, 90(4):626-627, 626 (Oct. 1985) ("Golding").

Wong, C. M., et al. "Percutaneous Left Ventricular Angiography." Catheter Cardio Diag, 7:425-432 (1981).

Lurie, Paul R., et al. "An Apical Technic for Catherization of the Left Side of the Heart Applied to Infants and Children." New Engl J Med, 264(23):1182-1187 (1961).

Maxwell, Darryl, et al. "Balloon Dilatation of the Aortic Valve in the Fetus: A Report of Two Cases." Br Heart J, 65:256-258 (1991).

Neish, Steven R., et al. "Intraoperative Balloon Valvuloplasty for Critical Aortic Valvular Stenosis in Neonates." Am J Cardiol, 68:807-810 (1991).

Tworetzky, Wayne, et al. "Balloon Dilation of Severe Aortic Stenosis in the Fetus: Potential for Prevention of Hypoplastic Left Heart Syndrome Candidate Selection, Technique, and Results of Successful Intervention." Circulation, 110:2125-2131 (2004).

Semple, T. "Left Heart Catherization by Direct Ventricular Puncture." Brit Heart J, 30:402-406 (1968).

Cribier, Alain, et al. Percutaneous Transluminal Valvuloplasty of Acquired Aortic Stenosis in Elderly Patients: An Alternative to Valve Replacement? Lancet, 1:63-67 (1986).

McKay, Raymond, G., et al. "The Mansfield Scientific Aortic Valvuloplasty Registry: Overview of Acute Hemodynamic Results and Procedural Complications." JACC, 17(2):485-491 (1991).

Bashore, Thomas, M., et al. "Follow-up Recatherization After Balloon Aortic Valvuloplasty." JACC, 17(5):1188-1195 (1991).

Cribier, Alain, et al. "Trans-Catheter Implantation of Balloon-Expandable Prosthetic Heart Valves: Early Results in an Animal Model." Circulation, 104(17), II-552:2609 (2001).

Zhou, Junqing. "Chirurgie Valvulaire Par Voie Endovasculaire." Thesis (2003) ("Zhou's Thesis").

Gott, Vincent L., et al. "Mechanical Heart Valves: 50 Years of Evolution." Ann Thorac Surg, 76:S2230-2239 (2003).

McClure, Scott R., et al. "Late Outcomes for Aortic Valve Replacement with the Carpentier—Edwards Pericardial Bioprosthesis: Up to 17-Year Follow-Up in 1,000 Patients." Ann Thorac Surg, 89:1410-1416 (2010).

Cribier, Alain, et al. "Percutaneous Transcatheter Implantation of an Aortic Valve Prosthesis for Calcific Aortic Stenosis: First Human Case Description." Circulation 106.24 (2002): 3006-3008.

McKay, Raymond G., et al. "Balloon Dilatation of Calcific Aortic Stenosis in Elderly Patients: Postmortem, Intraoperative, and Percutaneous Valvuloplasty Studies." Circulation,74.1 (1986): 119-125.

(56) References Cited

OTHER PUBLICATIONS

McKay, R. G., et al. "Assessment of Left Ventricular and Aortic Valve Function After Aortic Balloon Valvuloplasty in Adult Patients With Critical Aortic Stenosis." Circulation, 75.1 (1987): 192-203.
Block, Peter C., and Igor F. Palacios. "Comparison of Hemodynamic Results of Anterograde Versus Retrograde Percutaneous Balloon Aortic Valvuloplasty." The American Journal of Cardiology, 60.8 (1987): 659-662.
Neish, Steven R., et al. "Intraoperative Balloon Valvuloplasty for Critical Aortic Valvular Stenosis in Neonates." The American Journal of Cardiology, 68.8 (1991): 807-810.
Brock, Russell, et al. "Percutaneous left ventricular puncture in the assessment of aortic stenosis." Thorax, 11.3 (1956): 163-171.
Sanderud, A., and K. Rasmussen. "Preoperative Evaluation of the Aortic Orifice At Left Ventricular Puncture." Scandinavian Cardiovascular Journal,1.2 (1967): 138-141.
Wong, Philip HC, et al. "Aortic Catheterisation Via Percutaneous Left Ventricular Puncture." Catheterization and Cardiovascular Diagnosis, 9.4 (1983): 421-427.
Seldinger, Sven Ivar. "Catheter Replacement of the Needle in Percutaneous Arteriography A New Technique." Acta Radiologica 5 (1953): 368-376.
Webb, John G., et al. "Percutaneous Stent Mounted Valve for Treatment of Aortic or Pulmonary Valve Disease." Catheterization and Cardiovascular Interventions 63.1 (2004): 89-93.
Morgan, J. M., et al. "Left Heart Catheterization by Direct Ventricular Puncture: Withstanding the Test of Time." Catheterization and Cardiovascular Diagnosis, 16.2 (1989): 87.
Cata, C. J., et al. "Technique of Apical Left Ventricular Puncture Revisited: A Case Report of Double-Valve Prosthesis Evaluation." The Journal of Invasive Cardiology, 6.7 (1994): 251-255.

\* cited by examiner

ADAPTER FOR PROSTHESIS DELIVERY DEVICE AND METHODS OF USE

INCORPORATION BY REFERENCE TO ANY PRIORITY APPLICATIONS

This Application claims the benefit of U.S. Provisional Application Ser. No. 62/250,359, filed Nov. 3, 2015, titled "ADAPTER FOR PROSTHESIS DELIVERY DEVICE AND METHODS OF USE", and U.S. Provisional Application Ser. No. 62/383,132, filed Sep. 2, 2016, titled "ADAPTER FOR PROSTHESIS DELIVERY DEVICE AND METHODS OF USE", the entirety of each of which is incorporated herein by reference.

BACKGROUND

Field

Certain embodiments disclosed herein related to steerable adapters for delivery devices implanting prostheses within a lumen or body cavity. In particular, the delivery devices relate in some embodiments to replacement heart valves, such as replacement mitral heart valves.

Description of the Related Art

Human heart valves, which include the aortic, pulmonary, mitral and tricuspid valves, function essentially as one-way valves operating in synchronization with the pumping heart. The valves allow blood to flow downstream, but block blood from flowing upstream. Diseased heart valves exhibit impairments such as narrowing of the valve or regurgitation, which inhibit the valves' ability to control blood flow. Such impairments reduce the heart's blood-pumping efficiency and can be a debilitating and life threatening condition. For example, valve insufficiency can lead to conditions such as heart hypertrophy and dilation of the ventricle. Thus, extensive efforts have been made to develop methods and apparatuses to repair or replace impaired heart valves.

Prostheses exist to correct problems associated with impaired heart valves. For example, mechanical and tissue-based heart valve prostheses can be used to replace impaired native heart valves. More recently, substantial effort has been dedicated to developing replacement heart valves, particularly tissue-based replacement heart valves that can be delivered with less trauma to the patient than through open heart surgery. Replacement valves are being designed to be delivered through minimally invasive procedures and even percutaneous procedures. Such replacement valves often include a tissue-based valve body that is connected to an expandable frame that is then delivered to the native valve's annulus.

Development of prostheses including but not limited to replacement heart valves that can be compacted for delivery and then controllably expanded for controlled placement has proven to be particularly challenging. An additional challenge relates to the ability of such prostheses to be secured relative to intralumenal tissue, e.g., tissue within any body lumen or cavity, in an atraumatic manner.

Delivering a prosthesis to a desired location in the human body, for example delivering a replacement heart valve to the mitral valve, can also be challenging. Obtaining access to perform procedures in the heart or in other anatomical locations may require delivery of devices percutaneously through tortuous vasculature or through open or semi-open surgical procedures. The ability to control the deployment of the prosthesis and to provide control of the delivery device at the desired location can also be challenging.

SUMMARY

Embodiments of the present disclosure are directed to delivery systems, devices and/or methods of use to deliver and/or controllably deploy a prosthesis, such as but not limited to a replacement heart valve, to a desired location within the body. In some embodiments, a replacement heart valve and methods for delivering a replacement heart valve to a native heart valve, such as a mitral valve, are provided.

The present disclosure includes, but is not limited to, the following numbered embodiments.

Embodiment 1

An adapter configured to manipulate the position of a delivery system, the adapter comprising a clamp configured to at least partially hold a handle of the delivery system, a first actuator configured to provide translational motion of the clamp along a longitudinal axis of the handle of the delivery system, a second actuator configured to provide rotational motion of the clamp along a first rotational axis, and a third actuator configured to provide rotational motion of the clamp along a second rotational axis, wherein the first rotational axis is generally perpendicular to the second rotational axis.

Embodiment 2

The adapter of Embodiment 1 further comprising a mating component configured to releasably mate with a component outside of the adapter.

Embodiment 3

The adapter of any one of Embodiments 1-2 wherein the first actuator, the second actuator, and the third actuators are knobs.

Embodiment 4

The adapter of any one of Embodiments 1-3 wherein the first actuator is a knob connected to a screw and the clamp is configured to translate along the screw.

Embodiment 5

The adapter of any one of Embodiments 1-3 wherein the second and third actuators are knobs in communication with gears configured to provide the rotational motion.

Embodiment 6

The adapter of any one of Embodiments 1-5 further comprising a pair of U-shaped members, each U-shaped member attached to one of the second or third actuators, wherein the U-shaped members are configured to rotate with respect to one another to provide the rotational motion to the clamp.

Embodiment 7

A method for manipulating the position of a delivery system, the method comprising clamping a handle of the delivery system, actuating a first knob to translate the handle along a longitudinal axis of the handle, actuating a second knob to rotate the handle of the delivery system around a first rotational axis, and actuating a third knob to rotate the handle of the delivery system around a second rotational axis, the second rotational axis being generally perpendicular to the first rotational axis.

Embodiment 8

An adapter for manipulating the position of a handle of a delivery system, the adapter comprising a clamp configured to receive and retain the handle, an h-shaped bracket connected to the clamp, the h-shaped bracket having at least one knob configured to translate the clamp along a screw extending across opposing legs on the h-shaped bracket, a first U-shaped member fixedly attached to the h-shaped bracket, a second U-shaped member rotatably connected to the first U-shaped member, the first U-shaped member and second U-shaped member configured to be rotated independently of one another, and an adapter located on the second U-shaped member, the adapter configured to connect to an outside component.

Embodiment 9

The adapter of Embodiment 8, further comprising a plurality of knobs configured to rotate the first U-shaped member and the second U-shaped member.

Embodiment 10

The adapter of any one of Embodiments 8-9, wherein the clamp is configured to translate and/or rotate in three dimensions.

Embodiment 11

The adapter of any one of Embodiments 8-10, further comprising an x-shaped member connecting opposite legs of the first U-shaped member and opposite legs of the second U-shaped member, the x-shaped member acting as a rotation axis for rotation of the first U-shaped member with respect to the second U-shaped member.

Embodiment 12

An adapter for manipulating the position of a handle of a delivery system, the adapter comprising a clamp configured to receive and retain the handle, a u-shaped bracket connected with the clamp, the u-shaped bracket having at least one knob configured to translate the clamp along a screw extending between opposite ends of the u-shaped bracket, a first gear attached to u-shaped bracket and configured to be rotated, a first support platform rotatably attached to the first gear, a second gear fixedly attached to the first support platform and configured to be rotated, a second support platform rotatably attached to the second gear, and an adapter located on the second support platform, the adapter configured to connect to an outside component.

Embodiment 13

The adapter of Embodiment 12, further comprising a plurality of knobs configured to rotate the first gear and the second gear.

Embodiment 14

The adapter of Embodiment 13, further comprising a first secondary gear mating with one of the plurality of knobs and the first gear and a second secondary gear mating with one of the plurality of knobs and the second gear.

Embodiment 15

The adapter of any one of Embodiments 12-14, wherein the first and second support platforms are generally l-shaped.

Embodiment 16

The adapter of any one of Embodiments 12-15, wherein the clamp is configured to translate and/or rotate in three dimensions.

Embodiment 17

The adapter of any one of Embodiments 12-16, wherein the first gear is configured to rotate the clamp on a plane perpendicular to the plane created by rotation of the second gear.

Embodiment 18

An adapter configured to manipulate the position of a delivery system, the adapter comprising a clamp configured to at least partially hold a handle of the delivery system, a first actuator configured to provide translational motion of the clamp along a longitudinal axis of the handle of the delivery system, a ball and socket joint, wherein the ball and socket joint allows for angular movement of the clamp, and a locking system configured to prevent motion of the ball and socket joint when activated.

Embodiment 19

The adapter of Embodiment 18, wherein the locking system is a spring loading locking system comprising a locking plate configured to retain a ball in the ball and socket joint in place.

Embodiment 20

The adapter of Embodiment 18, further comprising an adapter configured to connect to an outside component.

Embodiment 21

The adapter of Embodiment 18, further comprising a plurality of legs configured to act as a stand for the adapter.

Embodiment 22

The adapter of Embodiment 18, wherein the clamp is configured to translate and/or rotate in three dimensions.

Embodiment 23

The adapter of Embodiment 5, wherein a first and a second gear are configured to provide the rotational motion.

Embodiment 24

The adapter of any one of Embodiments 1-6, wherein the clamp is configured to translate and/or rotate in three dimensions.

Embodiment 25

The adapter of Embodiment 6, further comprising an x-shaped member connecting opposite legs of a first U-shaped member and opposite legs of a second U-shaped member, the x-shaped member acting as a rotation axis for rotation of the first U-shaped member with respect to the second U-shaped member.

DETAILED DESCRIPTION

Figure 1:
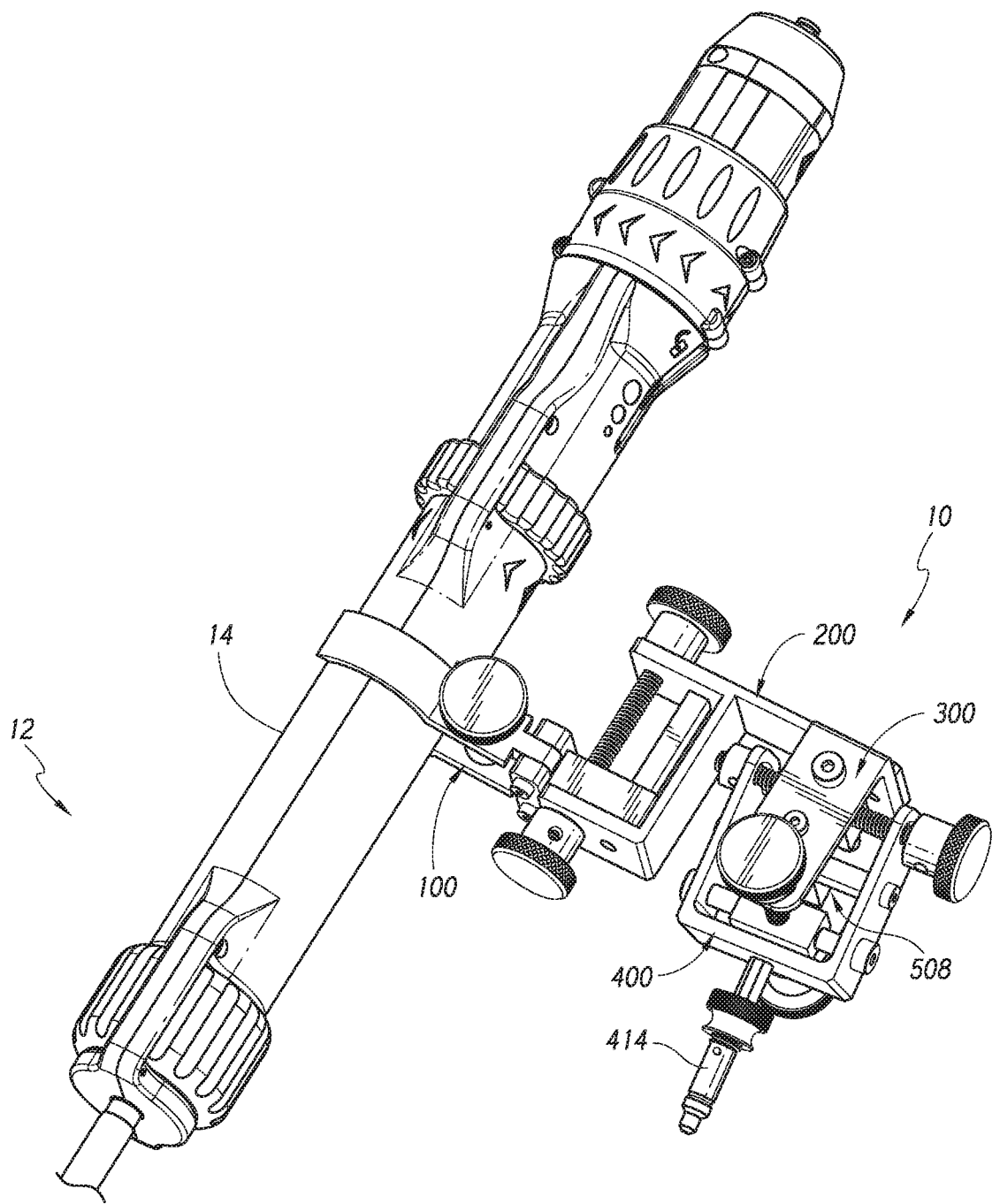
FIG. 1 shows a perspective view of an embodiment of a steerable adapter connected to a handle of a delivery system.

The present specification and drawings provide aspects and features of the disclosure in the context of several embodiments of replacement heart valves, delivery systems and methods that are configured for use in the vasculature of a patient, such as for replacement of natural heart valves in a patient. These embodiments may be discussed in connection with replacing specific valves such as the patient's aortic or mitral valve. However, it is to be understood that the features and concepts discussed herein can be applied to products other than heart valve implants. For example, the controlled positioning, deployment, and securing features described herein can be applied to medical implants, for example other types of expandable prostheses, for use elsewhere in the body, such as within an artery, a vein, or other body cavities or locations. In addition, particular features of a valve, delivery system, etc. should not be taken as limiting, and features of any one embodiment discussed herein can be combined with of the features of other embodiments as desired and when appropriate. While certain embodiments described herein are described in connection with a transapical delivery approach, it should be understood that these embodiments can be used for other delivery approaches such as, for example, transfemoral approaches. Moreover, it should be understood that certain of the features described in connection with some embodiments can be incorporated with other embodiments, including those which are described in connection with different delivery approaches. For example, the disclosed systems and methods can be used in conjunction with the disclosure of U.S. application Ser. No. 15/242,297, filed Aug. 19, 2016, entitled PROSTHESIS, DELIVERY DEVICE AND METHODS OF USE, and U.S. application Ser. No. 14/628,034, filed Feb. 20, 2015, entitled PROSTHESIS, DELIVERY DEVICE AND METHODS OF USE, the disclosures of both of which are hereby incorporated by reference in their entirety and should be considered a part of this specification.

During a replacement heart valve procedure, a physician may be required to hold a delivery system for the entire procedure and maintain the device position while reading the echo and fluoro imaging. With the weight of the delivery system and the length of the procedure, this is not a trivial task. If the delivery system is not held in the proper position then there is a potential for the prosthetic to be deployed in the incorrect location. Embodiments of the disclosed adapter allow the delivery system to be connected to a stabilization arm. With the delivery system connected to the stabilization arm, the physician can concentrate on achieving the desired location by focusing on the imaging rather than worrying about maintaining device position and fighting fatigue.

Generally, disclosed herein are attachment mechanisms or adapters that can be used to make precise motions on a delivery device, such as at the handle of the delivery device, in order to properly place a prosthesis or implant such as a replacement valve in a patient. The adapter can be configured to retain the delivery device handle, as discussed below, and can be attached to another piece of equipment in a hospital or laboratory setting as well. For example, embodiments of the disclosed adapters can be attached to a holding (or stabilization) arm, either manual or pneumatic, such as those produced by Aesculap® including, but not limited to, the RT040R pneumatic holding arm, the RT020R sterile drape adapter, the JG901 sterile drape, the Unitrac® air cartridge, and the RT090R table clamp. However, the particular piece of equipment that embodiments of the adapter are attached to is not limiting, and the adapter can be configured for attachment to any number of components.

In a typical surgical procedure, the holding arm can be attached to a surgery table prior to any surgical procedure, such as prior to the patient being brought in. However, the delivery system and adapter may not be attached to the holding arm until the distal end of the delivery system is introduced into a patient's heart and mitral annulus if being used for such a procedure. Once the distal end of the delivery system is in the proper location, the adapter holding the delivery system handle can be attached to the holding arm so that the delivery system can be manipulated as discussed below. The adapter can then be used until the valve is completely implanted and the delivery system is ready to be removed. At that time, the delivery system can be detached from the adapter and removed from the patient.

Embodiments of the disclosed adapters can provide a number of advantages. First, a physician using the delivery system would typically have to hold the delivery system for an extended period of time (~30 minutes in some cases) and thus fatigue would start to set in which would impact stabilization of the delivery system. Additionally, any small movement of the delivery system handle is amplified at the particular end location of the delivery system, such as at the mitral annulus. Thus, if the physician moves the handle a few millimeters, the distal end of the delivery system can move at least that distance, potentially more. Accordingly, using embodiments of the adapter attached to a holding arm can take these stability variables out of the equation and can allow the physician to focus on imaging, vitals, etc. and not have to worry about holding the delivery system steady.

Further, the adapter as discussed below allows for fine control/adjustment of the delivery system. During a typical procedure, the delivery system is angled very slightly in any direction as well as being adjusted axially by a millimeter or two at a time. Thus, it is very difficult for a physician to control these motions when holding it by hand. Therefore, embodiments of the disclosed adapter help stabilize the movements of the delivery system and make the movements more controlled and predictable.

Double U Block Steerable Adapter

Figure 2:
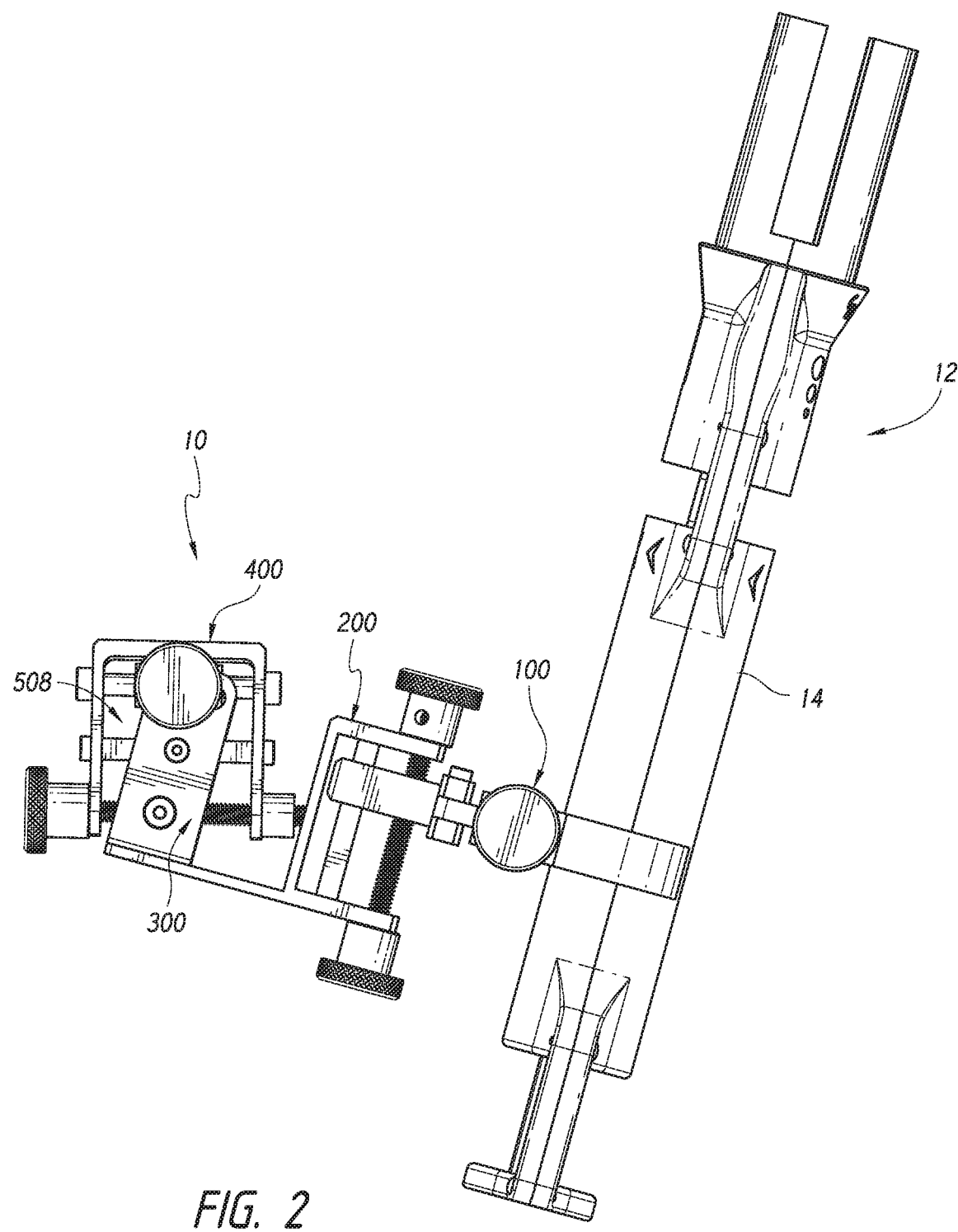
FIG. 2 shows a top-down view of the steerable adapter connected to the delivery system of FIG. 1.

FIG. 1 illustrates an embodiment of a steerable adapter 10 removably attached to the handle 14 of a delivery system 12. Starting nearest to the delivery system 12, the steerable adapter 10 can have a clamp 100. The clamp 100 can partially or fully surround the handle 14 of the delivery system 10 and can retain the handle 14 in a position desired by the user. FIG. 2 illustrates top down view of the steerable adapter 10 attached to the delivery system 12.

Figure 3:
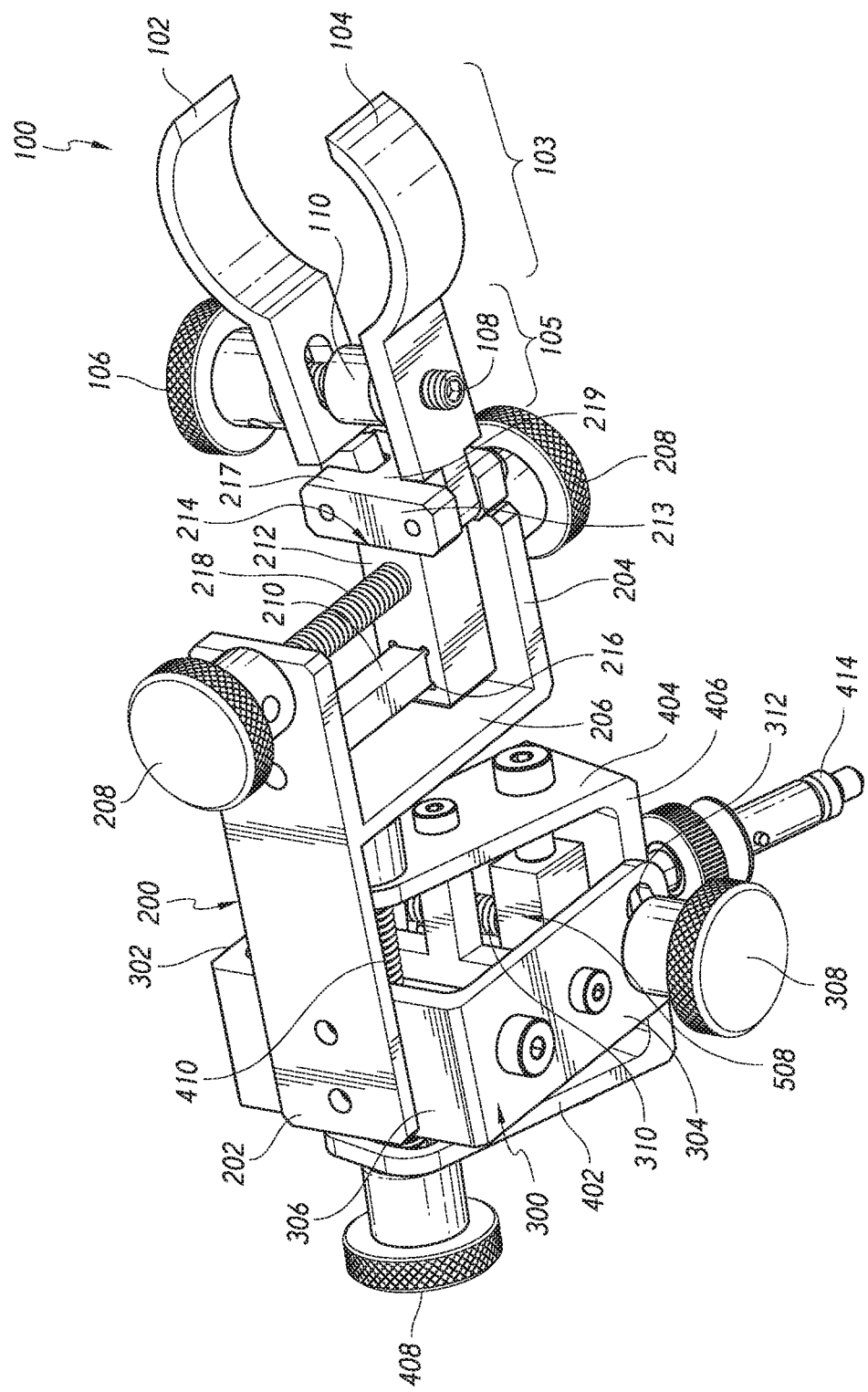
FIG. 3 shows a perspective view of the steerable adapter of FIG. 1.
Figure 4:
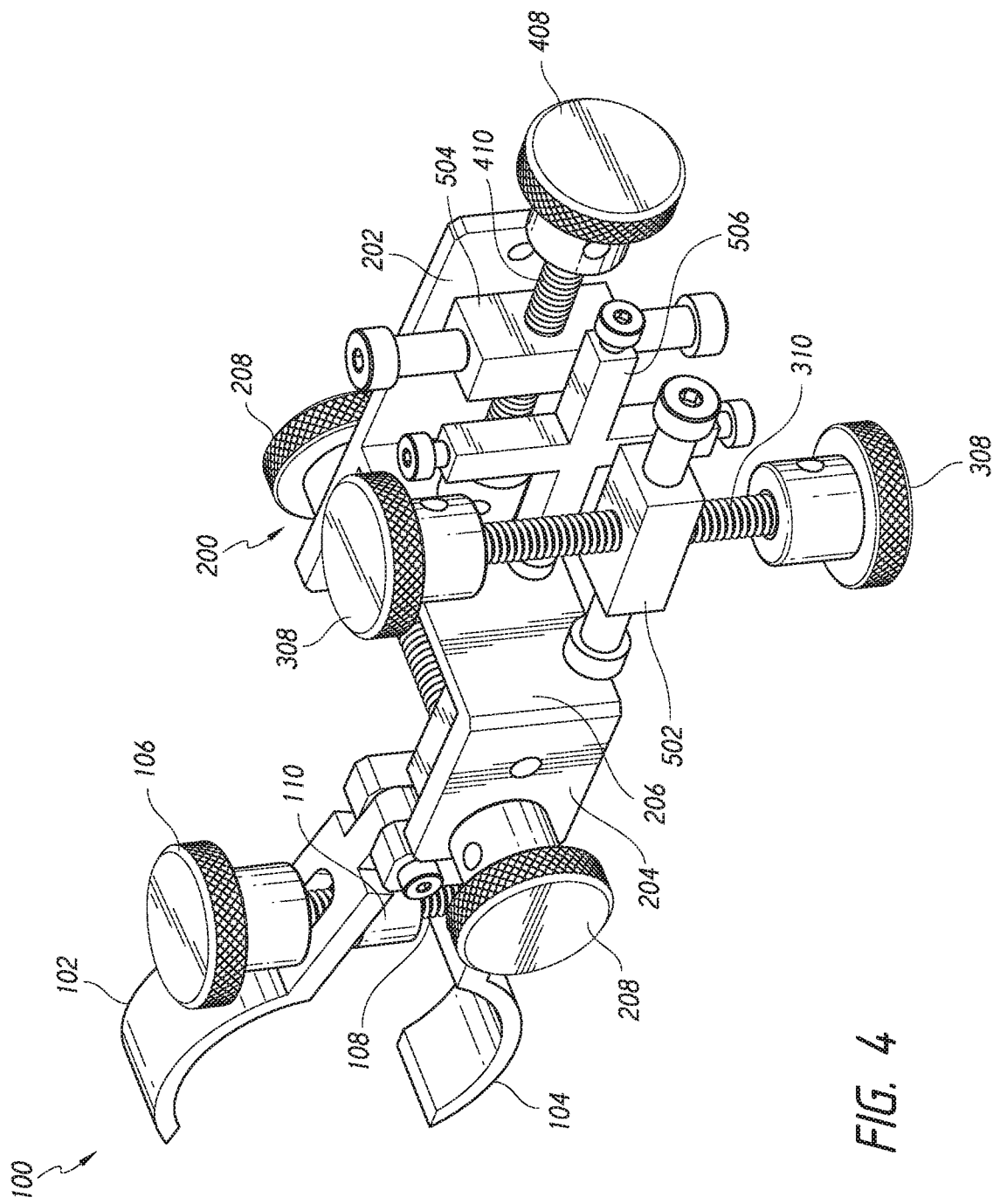
FIG. 4 shows the steerable adapter of FIG. 3 with U-shaped members removed to show internal components.
Figure 5:
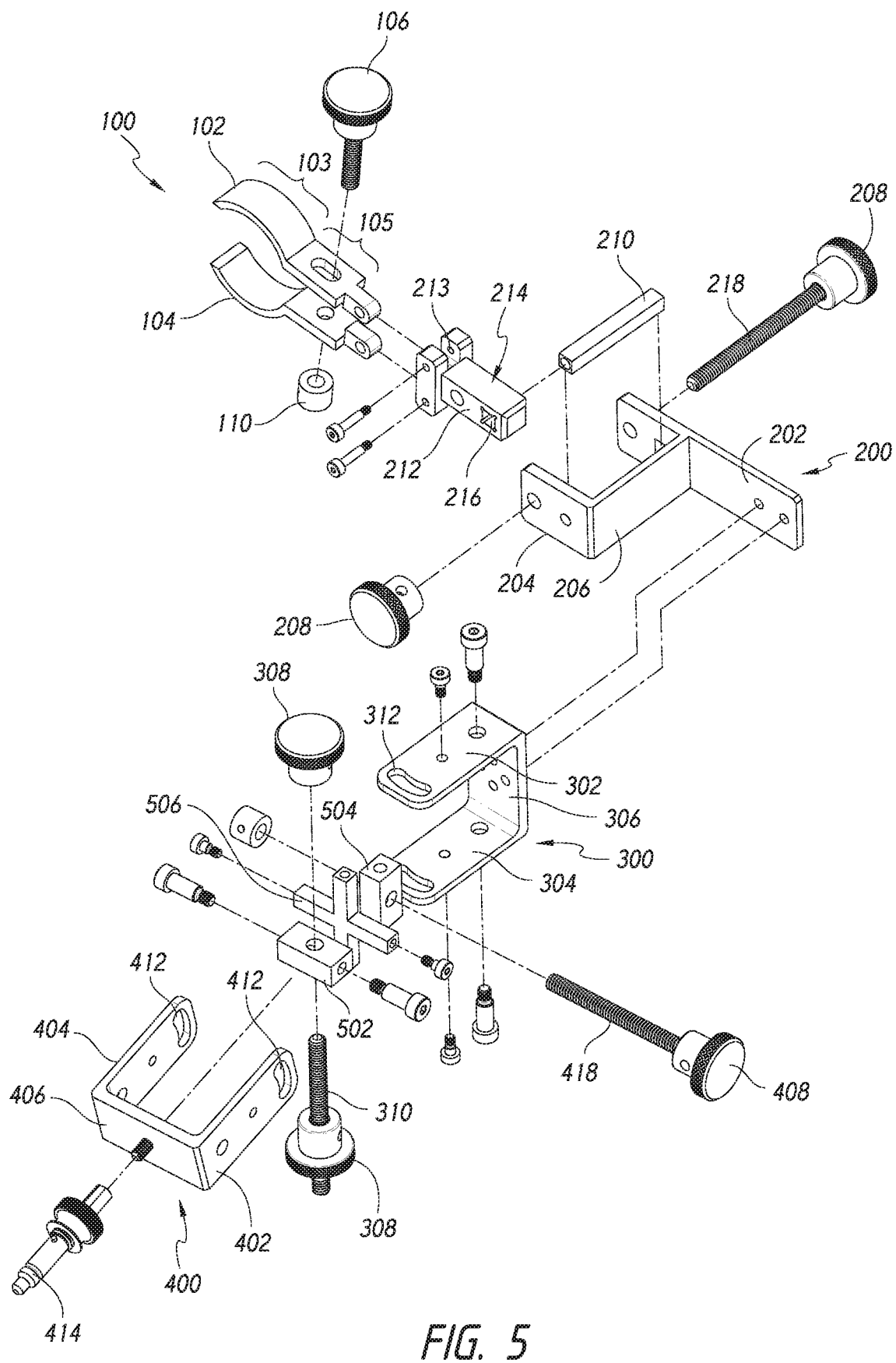
FIG. 5 shows an exploded view of the steerable adapter of FIG. 3.

As shown in FIGS. 3-5, clamp 100 itself can be made of an upper arm 102 and a lower arm 104 that can at least partially surround the handle 14 of the delivery system 12, though in other embodiments a single circular clamp, or other clamping/attachment mechanism, can be used. The arms 102/104 can be composed of generally c-shaped sections 103 facing one another. The c-shaped sections 103 can be attached to generally linear sections 105, though the particular shape can vary depending on the dimensions of the handle 14. The clamp 100 can further contain a knob 106 attached to a screw 108 which can pass through the two linear sections 105, though the particular location of the knob 106 and screw 108 is not limiting. Thus, a user can actuate the knob 106 to tighten or loosen the clamp 100. Further, a stopper 110 can be located on the screw 108 between the two linear sections 105. The stopper 110 can be generally cylindrical in shape and can prevent knob 106 from falling off the clamp 100 after screw 108 has completely disengaged from arm 104.

The clamp 100 can be generally translatably attached to an h-shaped member 200 (or chair member) through a series of components to be discussed. The h-shaped member 200 can consist of a long leg 202 opposite a short leg 204, with a connector leg 206 connecting an end of the short leg 204 and a midsection of the long leg 202 to form a lower case h (or chair-shaped) structure. The connector leg 206 can extend at approximately ⅓ of the length up the long leg 202, though the exact positioning is not limiting.

Further, knobs 208 can be located on the outside surface of the short leg 204 and the long leg 202 and connected to one another by a screw 218 passing through apertures in the short leg 204 and long leg 202. The screw 218 can run generally parallel to the connector leg 206, and thus perpendicular to the short leg 204 and the long leg 202.

Further, a guide block 210 can span between the inside surfaces of the short leg 204 and the long leg 202 and run generally parallel to the connector leg 206. As shown in FIG. 3, the guide block 210 can further be located farther from the clamp 100 than the knobs 208, but before the connector leg 206. The guide block 210 can be shaped generally like a rectangular prism, but the particular shape is not limiting.

Additionally, a T-shaped connector block 214 (shown in the exploded view of FIG. 5) can be located between the long leg 202 and the short leg 204. The T-shaped connector block 214 can be threadedly attached to the screw 218 through a threaded aperture in the T-shaped connector block 214. Further, the T-shaped connector block 214 can include an aperture 216 configured for the guide block 210 slides within. The aperture 216 can be approximately the same size as the guide block 210. Thus, the guide block 210 prevents rotation of the T-shaped connector block 214 upon turning of the knobs 208, though still allows for translational movement of the T-shaped connector block 214 along the screw 218.

The T-shaped connector block 214 can be made from a generally rectangular block 212 which is attached to the screw 218 and the guide block 210 as discussed above. At one end of the T-shaped connector block 214, nearest to the clamp 100, the rectangular block 212 can be attached to a generally clamp attachment block 213. The clamp attachment block 213 can be composed of two parallel extending arms 217 attached by a central arm 219, thus forming a capital H shape. Between the arms 217 are spaces in which the linear sections 105 of the clamp 100 can be inserted into so that they are rotatable within the clamp attachment block 213. In some embodiments, the linear sections 105 can include thinner flange portions to fit within the spaces in the arms 217. Accordingly, the clamp 100 can connect to the T-shaped connector block 214, thus allowing the clamp 100 to translate with the T-shaped connector block 214 upon rotation by knob 208 as well as rotate within the T-shaped connector block 214 to allow opening and closing of the clamp 100. Thus, the clamp 100 translates along the axis formed by the screw 218.

As shown in FIG. 3, opposite the clamp 100 side on the long leg 202, the h-shaped member 200 can be fixedly attached to a first U-shaped member 300. The first U-shaped member 300 can be composed of a top leg 302, a bottom leg 304 generally parallel to the top leg 302, and a connector leg 306 connecting the edges of the top leg 302 and bottom leg 304 to form a U shape. As shown, the long leg 202 of the h-shaped member 200 can be attached to the connector leg 306 of the U-shaped member 300 and can extend generally in the direction of the short leg 204 of the h-shaped member 200.

The first U-shaped member 300 can have a pair of knobs 308 (as shown in FIG. 4) attached to a screw 310 through a set of apertures 312 located on the ends of the bottom leg 304 and top leg 302, the apertures 312 located on the opposite side of the bottom leg 304 and top leg 302 from the connector leg 306. The apertures 312 can be sized to allow movement of the screw 310 within the apertures 312, as well as to allow partial rotation of the first U-shaped member 300 with respect to the screw 310.

A second U-shaped member 400 can be shaped generally the same as the first U-shaped member 300. The second U-shaped member 400 can be composed of a top leg 402, a bottom leg 404 generally parallel to the top leg 402, and a connector leg 406 connecting the top leg 402 and bottom leg 404 to form a U shape. The second U-shaped member 400 can have a knob 408 (or pair of knobs) attached to a screw 410 through a set of apertures 412 located on the ends of the bottom leg 404 and top leg 402, the apertures 412 located on the opposite side of the bottom leg 404 and top leg 402 from the connector leg 406. The apertures 412 can be sized to allow movement of the screw 410 within the apertures 412, as well as to allow partial rotation of the second U-shaped member 400 with respect to the screw 410. Further, the second U-shaped member 400 can have an mating component 414 located generally centrally on the connector leg 406 facing away from the U to allow for attachment of the steerable adapter 10 to another device such as, for example, a robotic arm.

Accordingly, as shown in FIG. 3, the first and second U-shaped members 300/400 are generally nestled within one another. Further, as shown in FIG. 1, the U-shaped members 300/400 can generally form walls around an internal area 508 (in a generally box-shape) including internal components discussed below.

The internal area 508 can include internal components within the U-shapes that allow for translation and rotation of the clamp 100 through actuation of the knobs 308 and 408 with respect to the mating component 414. The internal components are shown in FIG. 4 (with the first U-shaped member 300 and the second U-shaped member 400 removed for clarity). As shown, screw 310 can pass from the top and bottom legs 302/304 of the first U-shaped member 300 through a first U-shaped member translator block 502, which can be fixedly and rotatably connected to the inside surfaces of the top and bottom legs 402/404 of the second U-shaped member 400.

Similar to the first U-shaped member 300, the second U-shaped member 400 can include internal components within the U-shape to allow for movement of the clamp 100. First, the screw 410 can pass through the top 402 and bottom leg 404 of the second U-shaped member 400 through a second U-shaped member translator block 504, which can be fixedly and rotatably connected to the inside surfaces of the top and bottom legs 302/304 of the first U-shaped member 300, discussed below.

Additionally, an X-shaped block 506 can be rotatably connected to the inside of the top leg 302 and bottom leg 304 on opposite legs of the X-shaped block 506. The other two legs of the X-shaped block are also rotatably connected to the inside surfaces of the top leg 402 and bottom leg 404 of the second U-shaped member 400. The X-shaped block 506 acts as the rotation axis for respective motion of the first and second U-shaped members 300/400 with respect to one another. Accordingly, as knob 408 is rotated, translating second U-shaped member translator block 504, the first U-shaped member 300 rotates around an axis formed by the X-shaped block axis between the top and bottom legs 302/304 of the first U-shaped member 300. Thus, with respect to mating component 414, the first U-shaped member 300, the h-shaped block 212 and the clamp 100 move in a plane parallel to the top leg 302 of the first U-shaped member 300.

Similarly, as knob 308 is rotated, the second U-shaped member 400 rotates around an axis formed by the X-shaped block axis between the top and bottom legs 402/404 of the second U-shaped member 400. Thus, with respect to mating component 414, the first U-shaped member 300, the h-shaped block 212 and the clamp 100 move in a plane parallel to the top leg 402 of the second U-shaped member 400.

Accordingly, the disclosed particular configuration allows for rotation of the delivery system 12 in a plurality of directions by rotation of knobs 208, 308, and 408. Generally, the rotation of knob 208 will provide translational motion of the delivery system 12 along the longitudinal axis of the handle 14 of the delivery system 12. The rotation of knob 308 will provide rotational motion to the handle 14 along a plane parallel to the plane formed by arm 302 and rotation of knob 408 will provide rotational motion to the handle 14 along a plane parallel to the plane formed by arm 402. The two rotational planes will be generally perpendicular to one another as the X-shaped block 506 acts as the rotation axis for both rotational planes thus providing for two different planes of motion. These rotations of handle 14 will cause the tip of the delivery system 12 to move as well, providing for particular placement of a prosthesis in a patient's body. Thus, the combination of knobs 208, 308, and 408 can provide three dimensional motion of the delivery system 12.

Gear Steerable Adapter

Figure 6:
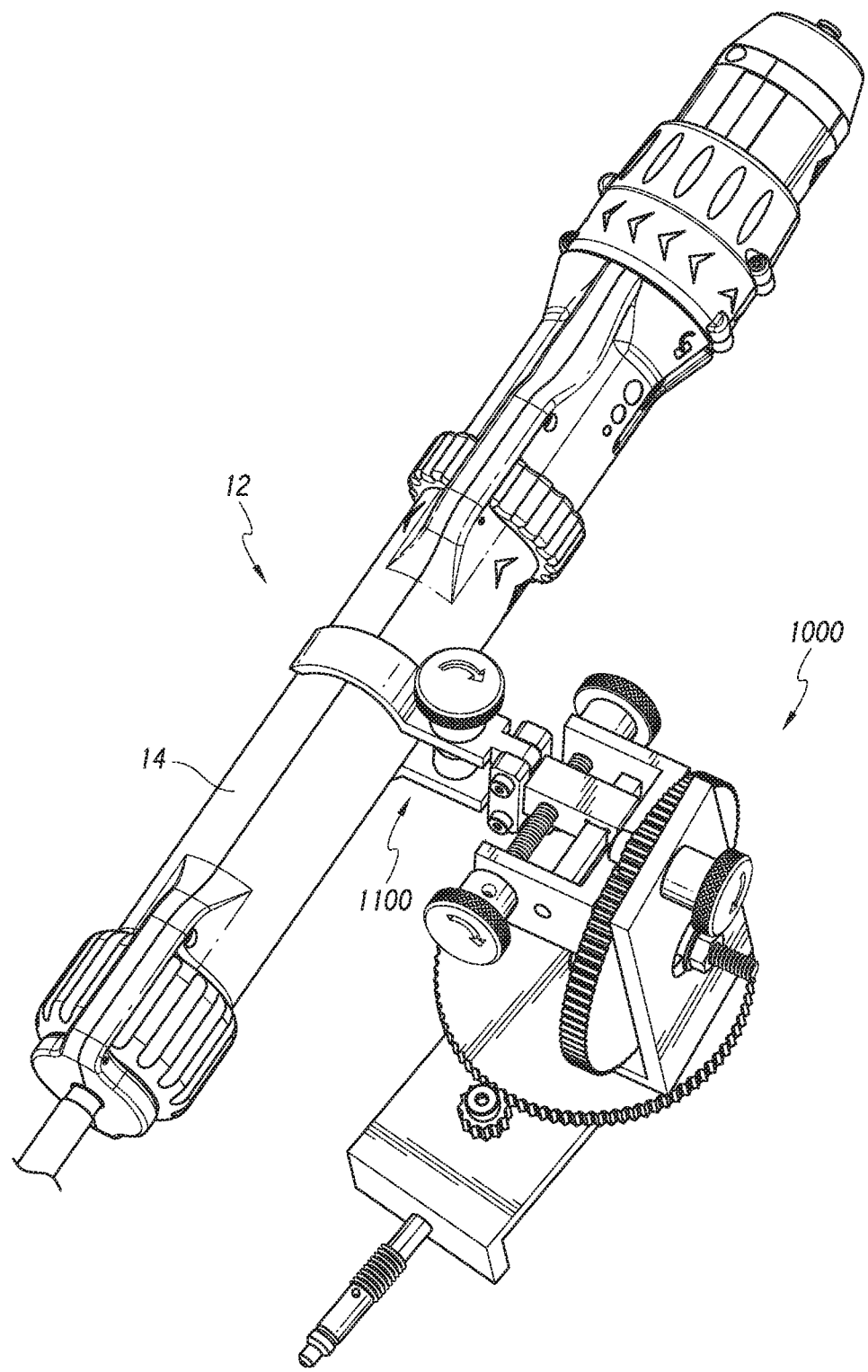
FIG. 6 shows a perspective view of another embodiment of a steerable adapter connected to a delivery system.

FIG. 6 illustrates another embodiment of a steerable adapter 1000 attached to the handle 14 of a delivery system 12. Starting nearest to the delivery system 12, the steerable adapter 1000 can have a clamp 1100. The clamp 1100 can partially or fully surround the handle 14 of the delivery system 10 and can removably retain the handle 14 in a position desired by the user.

Figure 7:
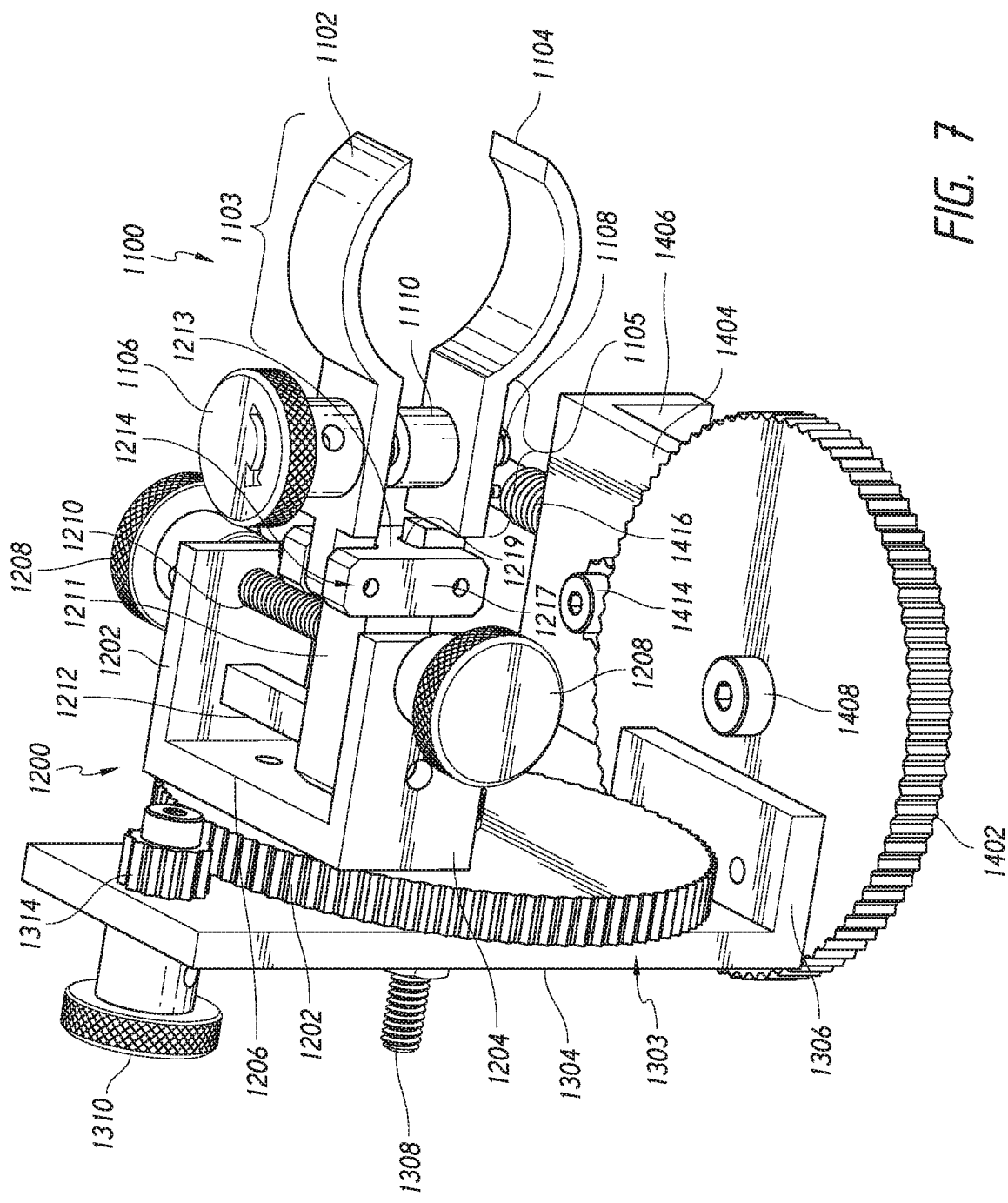
FIG. 7 shows a perspective view of the steerable adapter of FIG. 6 clamped to a delivery system.

As shown in FIG. 7, the clamp 1100 itself can be made of an upper arm 1102 and a lower arm 1104 that can at least partially surround the handle 14 of the delivery system 12, similar to what was described above, though in other embodiments a single circular clamp, or other clamping/attachment mechanism, can be used. The arms 1102/1104 can have generally c-shaped sections 1103 facing one another. The c-shaped sections 103 can be attached to linear sections 1105, though the particular shape can vary depending on the dimensions of the handle 14.

The clamp 1100 can further contain a knob 1106 attached to a screw 1108 which can pass through the two linear sections 1105, though the particular location of the knob 1106 and screw 1108 is not limiting. Thus, a user can actuate the knob 1106 to tighten or loosen the clamp 1100. Further, a stopper 1110 can be located on the screw 1108 between the two linear sections 1105. The stopper 1110 can be generally cylindrical in shape and can prevent knob 1106 from falling off the clamp 1100 after screw 1108 has completely disengaged from arm 1104.

The clamp 1100 can be generally translatably attached to a U-shaped member 1200. The U-shaped member 1200 can consist of a first leg 1202 opposite a second leg 1204, with a connector leg 1206 connecting the first leg 1204 and second leg 1202 to form a U structure. Knobs 1208 can be located on the outside surface of the second leg 1204 and the first leg 1202 and connected to one another by a screw 1220. The screw 1210 can run generally parallel to the connector leg 1206. The knobs 1208 can be located near the edges by the clamp 1100.

Further, a guide block 1212 can span between the inside surfaces of the second leg 1204 and the first leg 1202 and run generally parallel to the connector leg 1206. As shown in FIG. 7, the guide block 1212 can further be located farther from the clamp 1100 than the knobs 1208. The guide block 1212 can be shaped generally like a rectangular prism, but the particular shape is not limiting.

Figure 9:
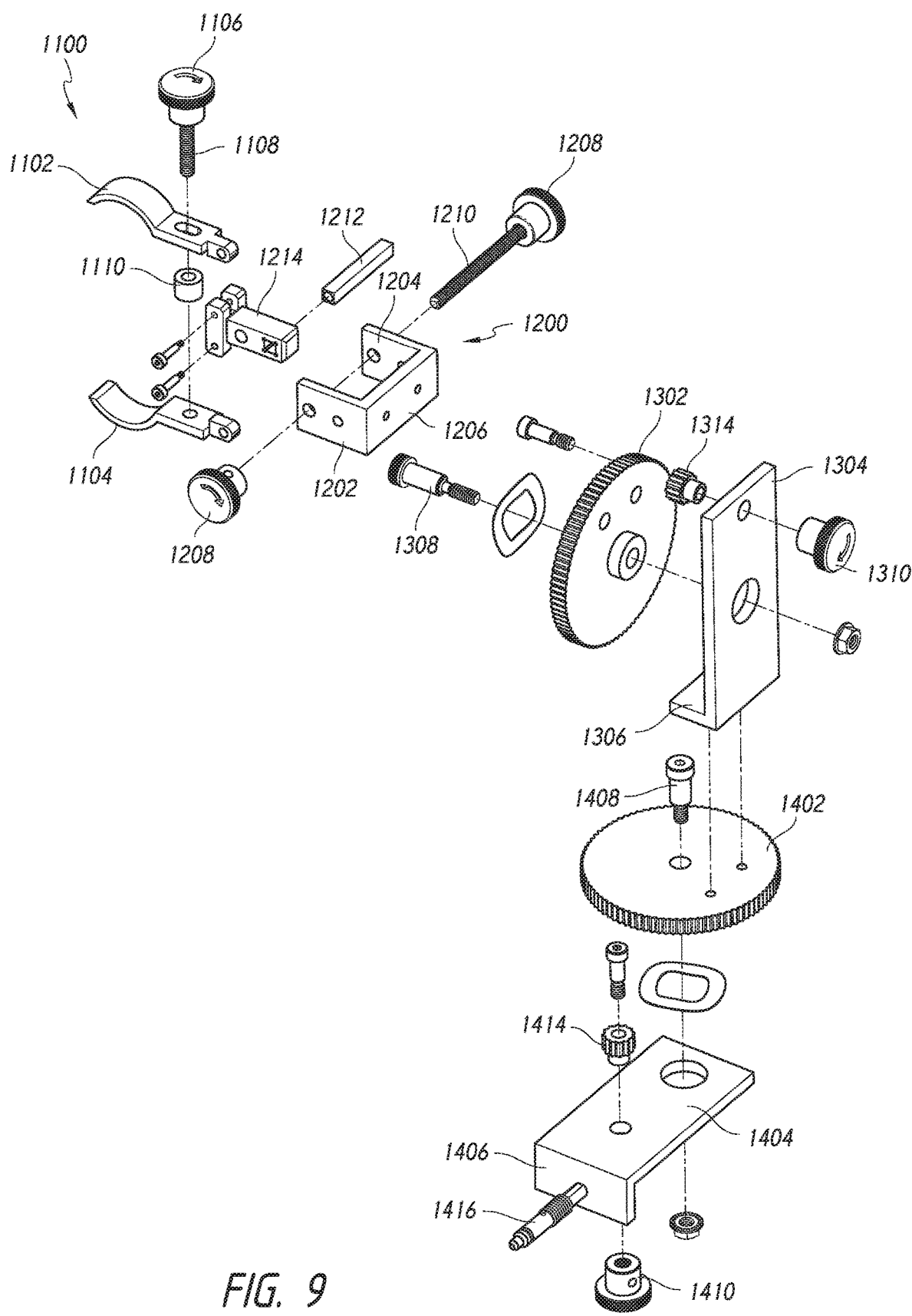
FIG. 9 shows an exploded view of the steerable adapter of FIG. 8.
Figure 10:
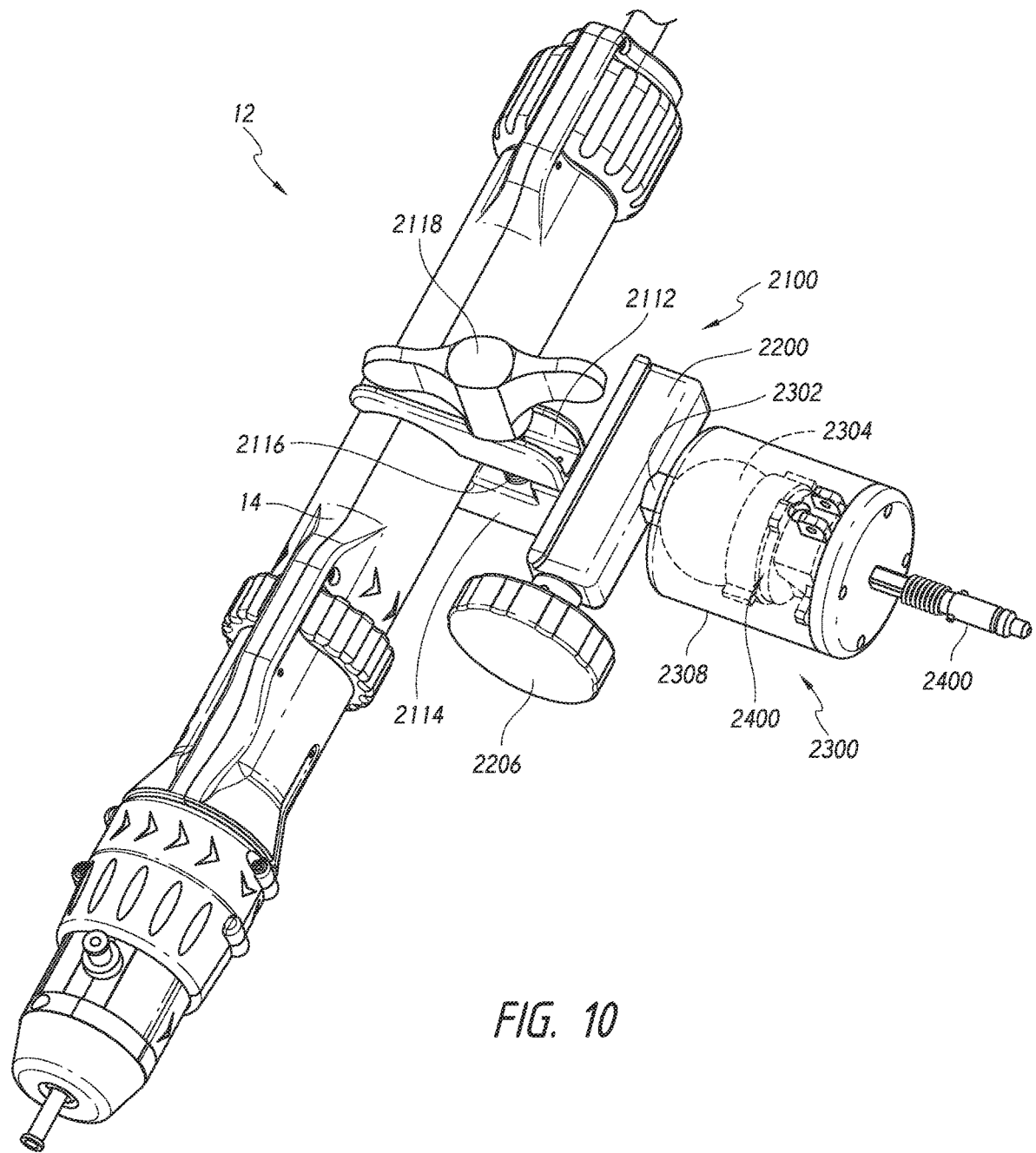
FIGS. 10-17 illustrate an embodiment of a steerable adapter.
Figure 11:
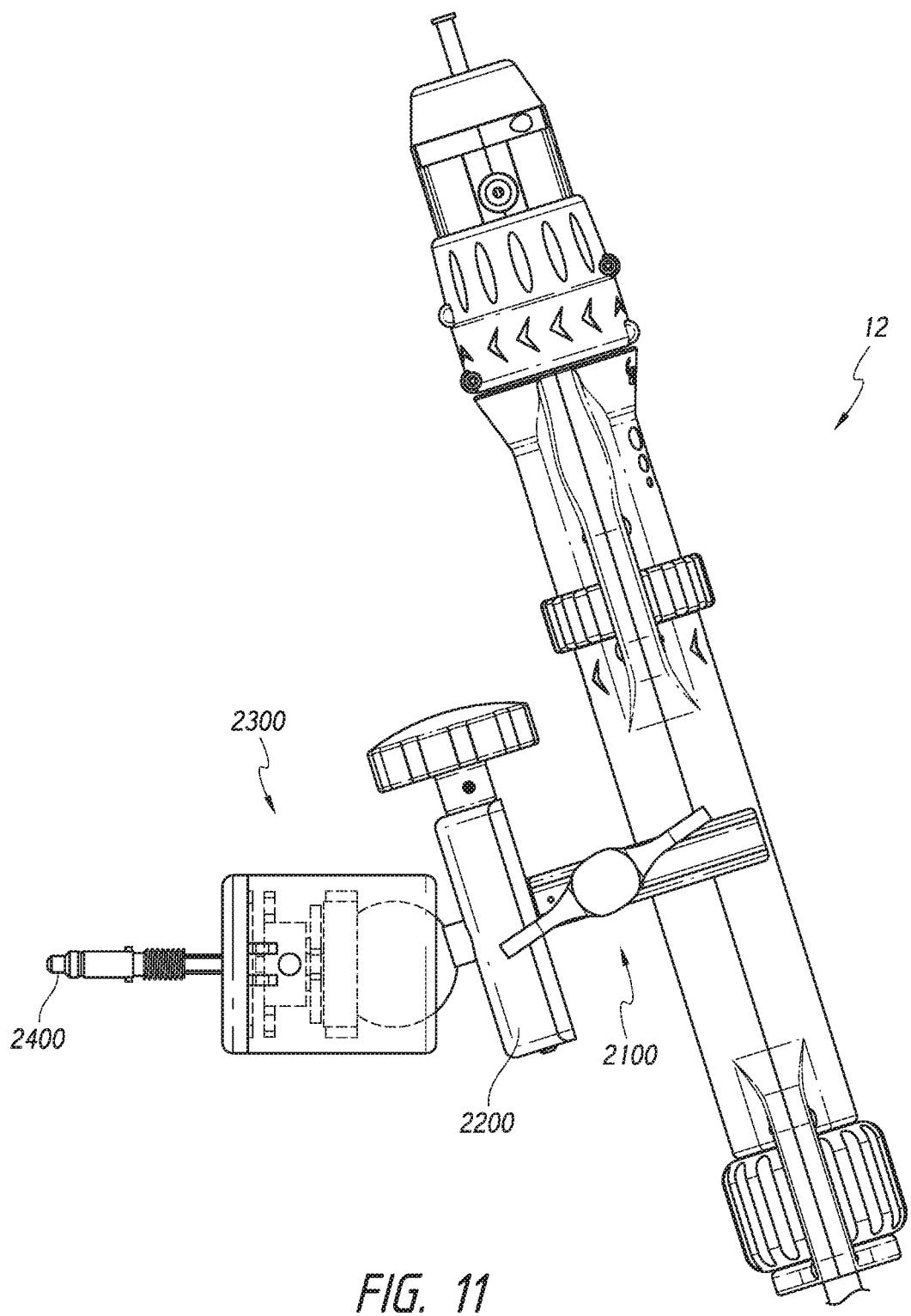

Additionally, a T-shaped connector block 1214 (shown in the exploded view of FIG. 9) can be located between the first leg 1202 and the second leg 1204. The T-shaped connector block 1214 can be threadedly attached to the screw 1210 through a threaded aperture in the T-shaped connector block 1214. Further, the T-shaped connector block 1214 can include an aperture configured so the guide block 1212 slides within. The aperture can be approximately the same size as the guide block 1212. Thus, the guide block 1212 prevents rotation of the T-shaped connector block 1214 upon turning of the knobs 1208, though still allows for translational movement of the T-shaped connector block 1214. The clamp 1100 can connect to the T-shaped connector block 1214, thus allowing the clamp 1100 to translate with the T-shaped connector block 1214 upon rotation by knob 1208.

The T-shaped connector block 1214 can be made from a generally rectangular block 1211 which is attached to the screw 1210 and the guide block 1212 as discussed above. At one end of the T-shaped connector block 1214, nearest to the clamp 1000, the rectangular block 1211 can be attached to a generally h-shaped block 1213. The h-shaped block 1213 can be composed of two parallel extending arms 1217 attached by a central arm 1219, thus forming a capital H shape. Between the arms 1219 are spaces in which the linear sections 1105 of the clamp 1000 can be inserted into so that they are rotatable within the U-shaped member 1200. In some embodiments, the linear sections 1105 can include thinner flange portions to fit within the spaces in the arms 1217. Accordingly, the clamp 1000 can connect to the T-shaped connector block 1214, thus allowing the clamp 1000 to translate with the T-shaped connector block 1214 upon rotation by knob 1208 as well as rotate within the T-shaped connector block 1214 to allow opening and closing of the clamp 1000. Thus, the clamp 1000 translates along the axis formed by the screw 1210.

The connector leg 1206 can be connected to a clamp gear 1302 on the side opposite from the clamp 1100. The connector leg 1206 can be attached to a face of the clamp gear 1302, though in some embodiments it can be connected to the outer rim of the clamp gear 1302 as well. Thus, the connector leg 1206, and accordingly clamp 1100, will rotate along with the rotation of the clamp gear 1302.

Opposite the U-shaped member 1200, the gear can be connected to a generally L-shaped first support wall 1303 formed of a large end 1304 and a short end 1306. In particular, the clamp gear 1302 can be connected to the large end 1304. For example, a screw 1308 can go through the center of the clamp gear 1302 and through the first support wall 1303 to mount the clamp gear 1302 to the first support wall 1303 will still retaining rotational motion.

Further, the first support wall 1303 can have a knob 1310 located on the opposite side of the first support wall 1303 from the clamp gear 1302. The knob 1301 can be connected to a screw 1312 passing through the first support wall 1303 to a clamp knob gear 1314 located on the same side of the first support wall 1303 as the clamp gear 1302. The clamp knob gear 1314 can have teeth that mate with the clamp gear 1302. Thus, rotation of the knob 1310 will rotate both the clamp knob gear 1314 and the clamp gear 1302. The clamp knob gear 1314 can be significantly smaller than the clamp gear 1302, thus allowing a user to make very minor adjustments through the rotation of the knob 1310.

Figure 8:
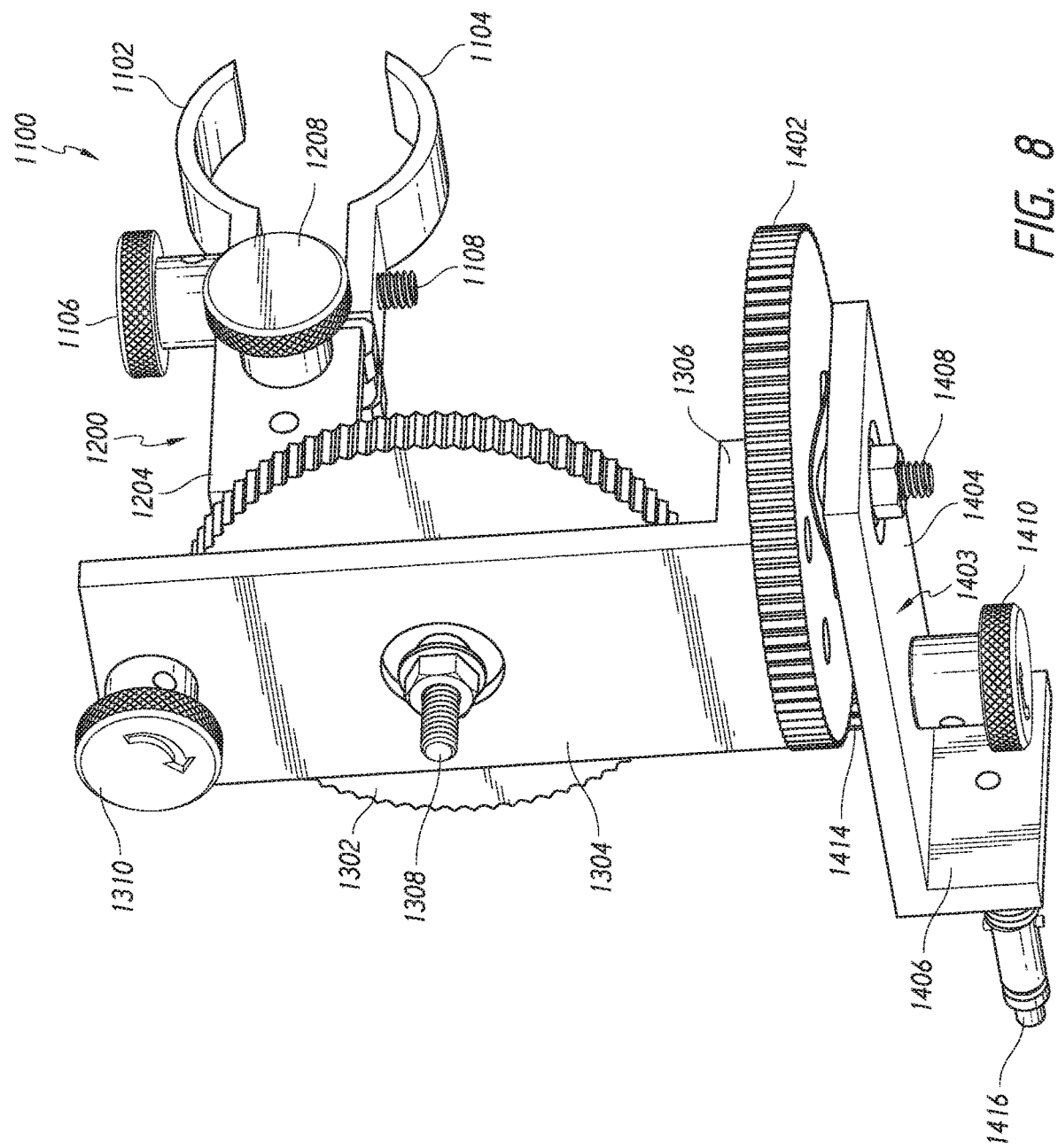
FIG. 8 shows a perspective view of the steerable adapter of FIG. 6 with the delivery system removed.

As mentioned, the support wall 1303 can be formed of a large end 1304 and a short end 1306. The short end 1306 can extend generally perpendicular from an end of the large end 1304. As shown in FIG. 8, the short end 1306 can be attached to the face of an adapter gear 1402, and thus rotation of the adapter gear 1402 will rotate the support wall 1303.

Opposite the short end 1306 of the first support wall 1303, the adapter gear 1402 can be connected to a generally L-shaped second support wall 1403 formed of a large end 1404 and a short end 1406. In particular, the adapter gear 1402 can be connected to the large end 1404. For example, a screw 1408 can go through the center of the adapter gear 1402 and through the second support wall 1403 to mount the clamp gear 1402 to the second support wall 1403 will still retaining rotational motion.

Further, the second support wall 1403 can have a knob 1410 located on the opposite side of the second support wall 1403 from the adapter gear 1402. The knob 1401 can be connected to a screw 1412 passing through the second support wall 1403 to an adapter knob gear 1414 located on the same side of the second support wall 1403 as the adapter gear 1402. The adapter knob gear 1414 can have teeth that mate with the adapter gear 1402. Thus, rotation of the knob 1410 will rotate both the adapter knob gear 1414 and the adapter gear 1402. The adapter knob gear 1414 can be significantly smaller than the clamp gear 1402, thus allowing a user to make very minor adjustments through the rotation of the knob 1410.

Further, the short end 1406 of the second support wall 1403 can have a mating component 1416 located on the short end 1406 facing away from the knob 1410 to allow for attachment of the steerable adapter 1000 to another device such as, for example, a robotic arm.

Thus, actuation of the different knobs 1106/1208/1310 will cause translation of the delivery system 12 held within the clamp 1100. For example, rotation of knob 1106 will cause translational motion of the delivery system 12 along the longitudinal axis of the handle 14 of the delivery system. Rotation of knob 1310 will cause the handle 14 to rotate in the plane of gear 1302 along with gear 1302. Rotation of knob 1410 will cause the handle 14 to rotate in the plane of gear 1402 along with gear 1402. As shown in FIG. 8, gear 1302 and 1402 are generally perpendicular to each other, thus providing for two different planes of motion. These rotations of handle 14 will cause the tip of the delivery system 12 to move as well, providing for particular placement of a prosthesis in a patient's body. Thus, the combination of knobs 1106/1208/1310 can provide three dimensional motion of the delivery system 12.

In addition, for the embodiments discussed above, there can be a further inclusion of additional knobs or other mechanisms for translating in different directions. For example, further knobs and screws can be used to provide additional translational motion outside of the translational motion discussed above. The additional knobs can allow for "sideways" and "up-and-down" motions, e.g., perpendicular to the translational motion discussed above, along with the different rotational motions discussed. Thus, if the current translational motion described above is along the x axis, additional knobs can be used to allow for translation along the y and z axes. Accordingly, the translational motion in the y and z axes is in addition to the movement described above, which may be considered to be the translation in the x axis and rotation within the x-y and x-z planes. This can allow for more flexibility of motion when using embodiments of the adapter.

Ball and Socket Adapter

Disclosed herein are embodiments of adapters that can incorporate a ball and socket joint. This can allow for more direct movement in the positioning of the delivery system within a patient, in particular in three dimensions, and can allow for a wide range of motion and control. Embodiments of the ball and socket adapters can be used in a similar manner as the adapters discussed in detail above.

Figure 12:
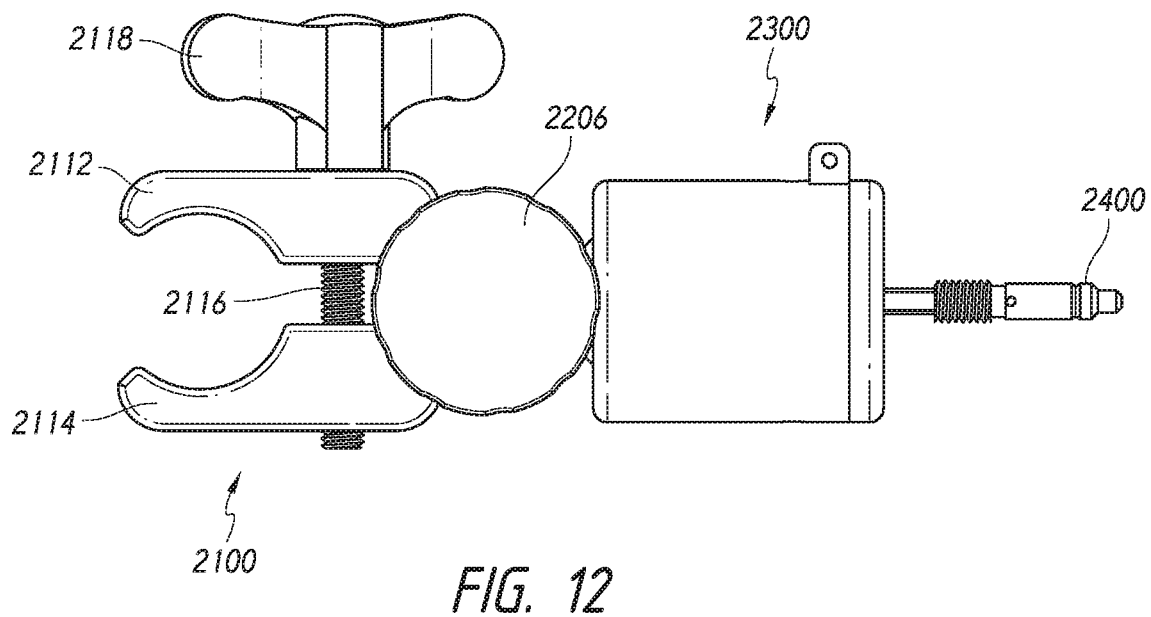
Figure 13:
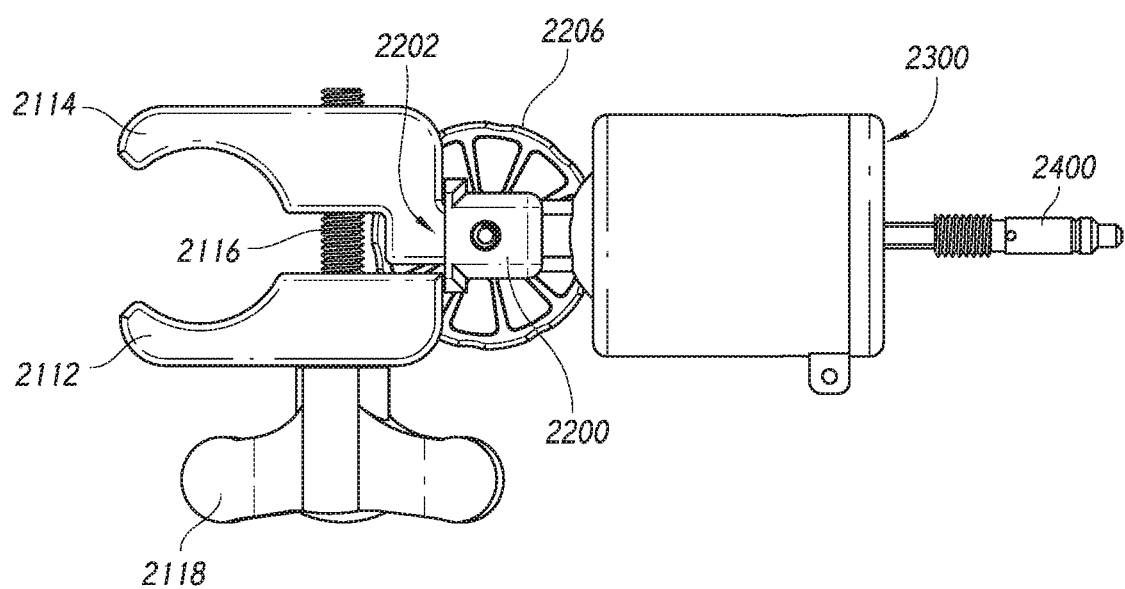
Figure 14:
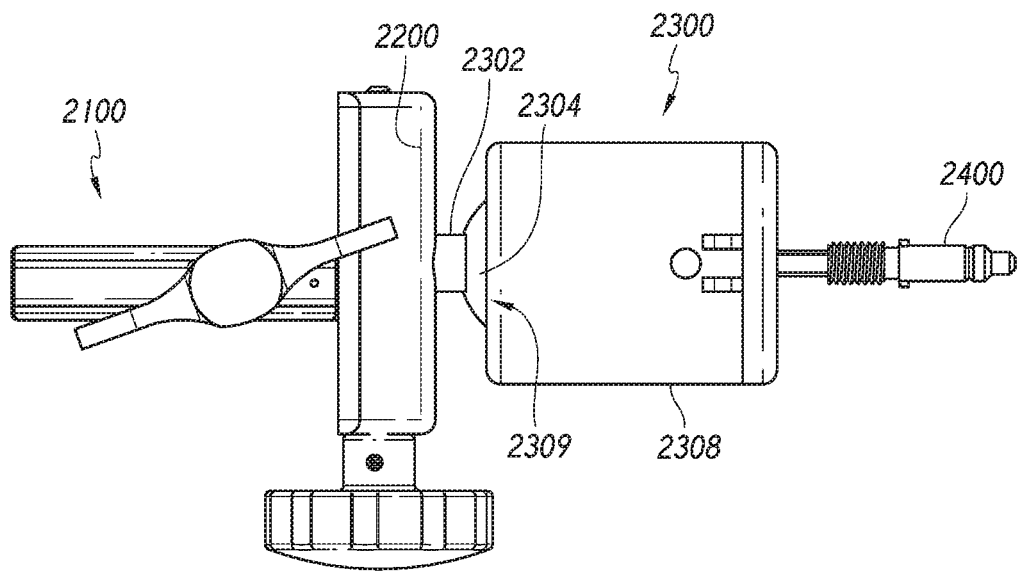
Figure 15:
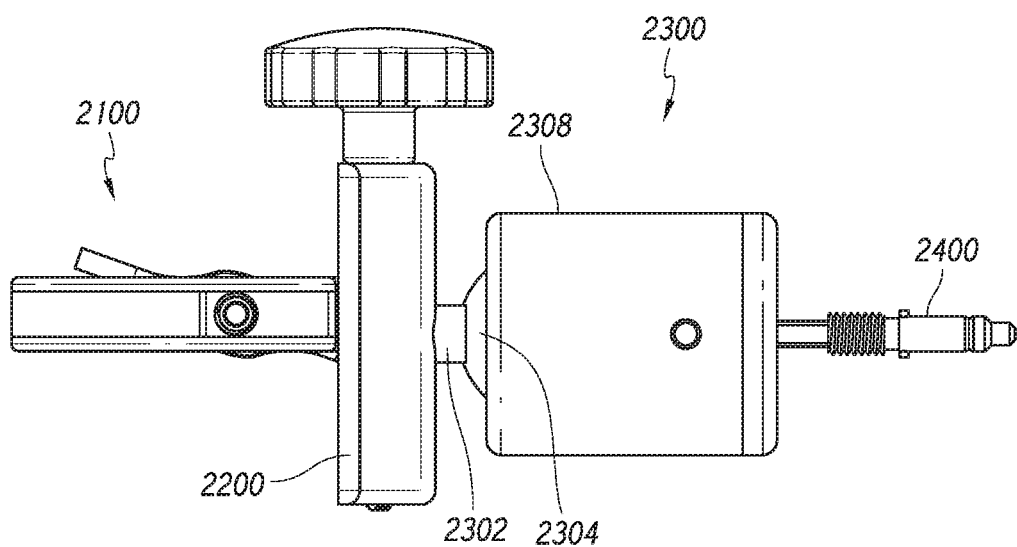
Figure 18:
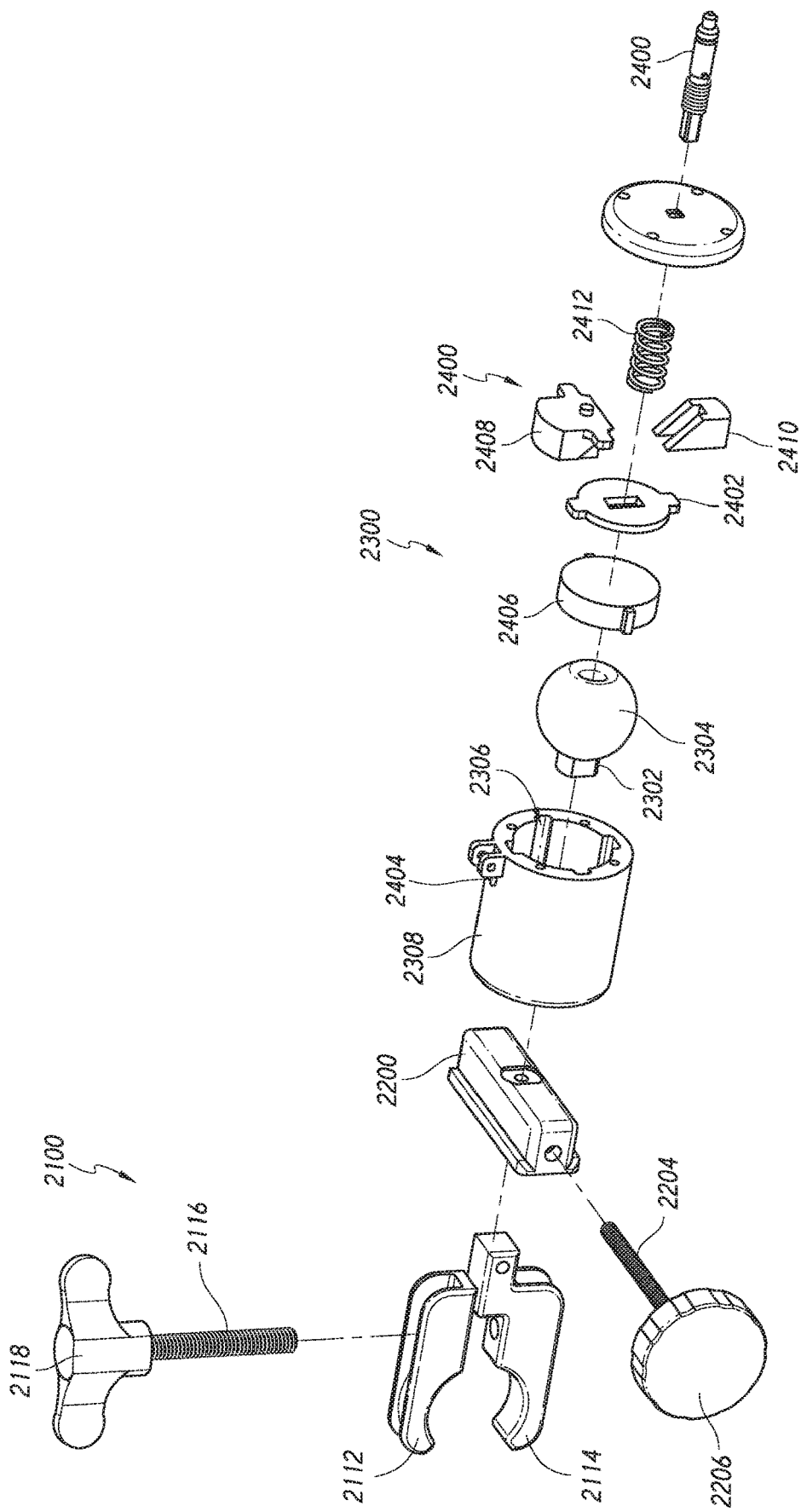
FIG. 18 illustrates an exploded view of the steerable adapter of FIG. 10-17.

FIGS. 10-18 illustrate an embodiment of a ball and socket adapter 2000 with FIG. 18 showing an exploded view. As shown, the adapter 2000 can have a clamp 2100 which is configured to releasably retain the handle 14 of a delivery system 12, such as detailed above. The clamp 2100 can be formed of a two pieces, such as top piece 2112 and a bottom piece 2114 attached together by a screw 2116 as shown in FIG. 12. In some embodiments, the two pieces can be integrally formed as a single piece, or can alternatively be formed from more pieces. As shown, the clamp 2100 can be configured to conform to the handle 14 in order to hold the handle 14 in place. Further, the clamp 2100 can be tightened or released, such as by turning knob 2118 attached to screw 2116 as required to adjust the positioning of the handle 14.

Figure 16:
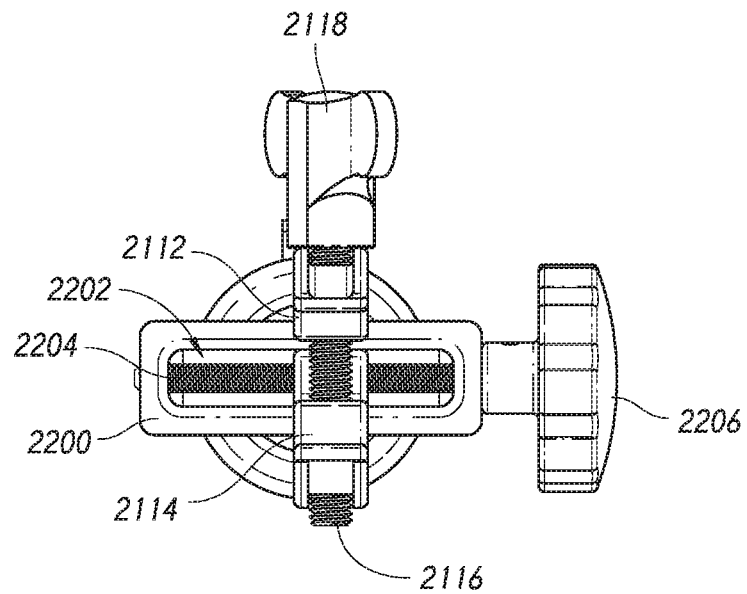
Figure 17:
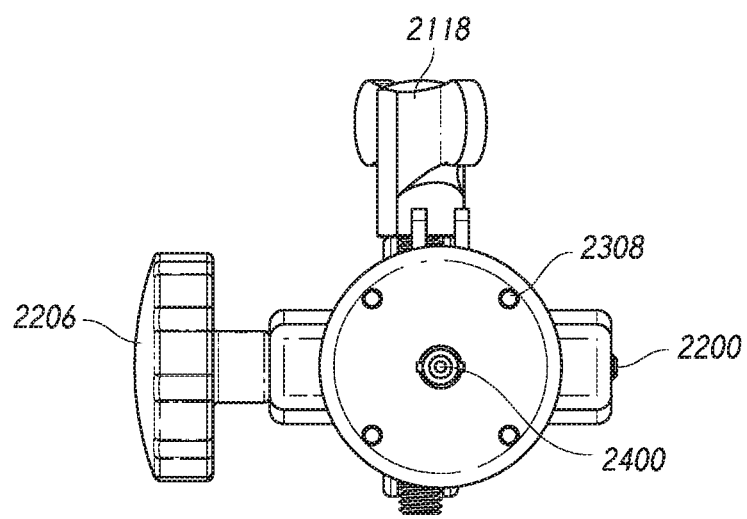

As shown in FIG. 16, the bottom piece 2114 of the clamp 2100 can include a portion to be inserted into a slot 2202 in a linear guide element 2200. A screw 2204 can be inserted through the linear guide element 2200 and into an aperture in the bottom piece 2114 of the clamp 2100. A knob 2206 can be used to turn the screw 2204, which can translate the clamp 2100 linearly along the slot 2202 of the linear guide element 2200. The walls of the linear guide element 2200 can prevent the clamp 2100 from rotating while the screw 2204 is being turned, and thus only provides linear motion.

This linear motion can position the handle 14 more atrial or more ventricular as needed during a replacement heart procedure.

Opposite of the slot 2202 in the linear guide element 2200, the linear guide element 2200 can be fixedly attached to a ball and socket joint 2300. As shown, the linear guide element 2200 can be attached to a tab 2302 connected to the ball 2304 within a housing 2308 in the ball and socket joint 2300. The ball 2304 can be allowed to freely rotate within a cavity 2306 in the housing 2308 of the joint 2300. The cavity 2306 can have an aperture located on the outer surface that allows the ball 2304 to rotate with constraints, allowing the delivery system 12 to be maneuvered in three different dimensions. This allows the system 12 to be angulated relative to a pneumatic arm that it is mated to.

As shown, the housing 2308 is generally cylindrical in shape, though other shapes can be used as well and the shape is not limiting.

The joint 2300 also contains a locking mechanism 2400 for preventing motion of the joint 2300, and thus the delivery system 12. As shown, the locking mechanism 2400 can include a spring loaded plate 2406 configured to be in a locked or unlocked position When in the locked position, the plate 2406 can prevent the ball 2304 from freely moving with gravity. For example, a spring 2412 can push on the plate 2406 to provide a frictional or mechanical force on the ball 2304 preventing motion. In some embodiments, the plate 2406 can include a tab configured to mate with a receiving surface on the ball 2304, thus locking it in place. A user may deactivate the spring 2412 to allow for manipulation and reengage the spring 2412 for locking. The plate 2406 can follow only internal grooves in the housing 2308 so as not to rotate.

The locking and unlocking of the ball 2304 can be caused by components shown in FIG. 18 which are stabilizing component 2402, first component 2408 and second component 2410. When locked, the spring 2412 can apply a force onto the first component 2408 which applies pressure to the pressure plate 2406, thereby locking the ball 2304 in place. The ball 2304 is unlocked by applying pressure to the second component 2410 through the apertures 2404 in the housing 2308. There can be one, two, three, four or five aperture 2404 in the housing 2308 and the number of apertures is not limiting. This pressure can cause the second component 2410 to compress the first component 2408, and thus the spring 2412, allowing the ball 2304 to freely rotate. Further, stabilizing component 2402 can ensure that the second component 2410, when compressed, acts on the first component 2408 instead of apply pressure to the pressure plate 2406.

However, other locking mechanisms can be used and the particular locking mechanism is not limiting.

Opposite of the aperture 2309 on the housing 2308 is a mating component 2400. The mating component 2400 can be located generally centrally on the housing 2308 to allow for attachment of the adapter 2000 to another device such as, for example, a robotic arm.

Figure 19:
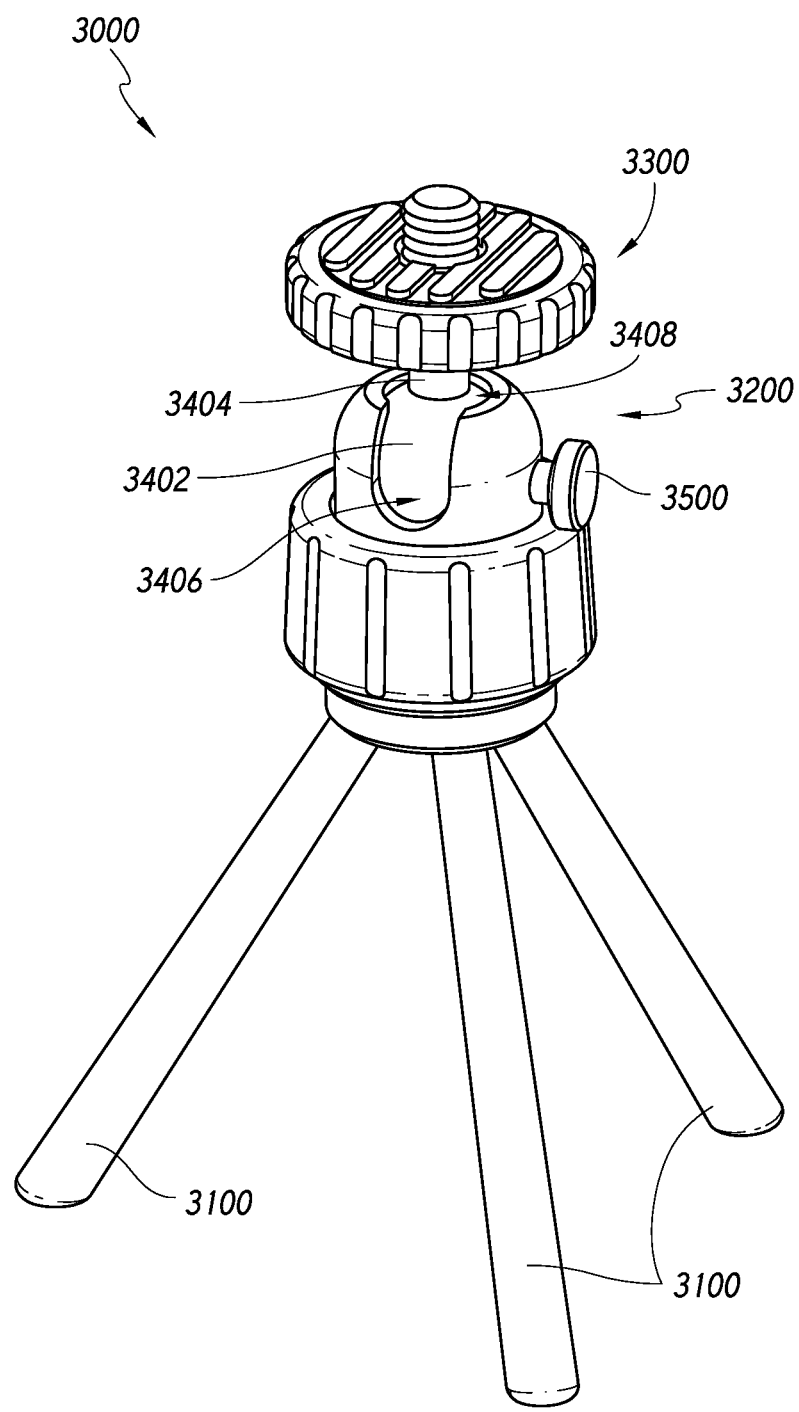
FIG. 19 illustrates an embodiment of a steerable adapter.

FIG. 19 shows an alternative embodiment of a ball and socket adapter 3000, which allows similar manipulation as those shown above. As shown in FIG. 19, the ball and socket adapter 3000 can include a number of legs 3100, a joint 3200, and a delivery system attachment mechanism 3300 configured to mate with a delivery system 12 or with any of the adapters/components discussed in detail above.

At its bottom, the ball and socket adapter 3000 can include a number of different legs 3100. While three legs 3100 are shown in FIG. 19, it will be understood that any number of legs can be used, such as 4, 5, 6, 7, or 8 legs. The legs 3100 can be articulable with respect to the joint 3200 so that their positions can be adjusted with respect to one another. The legs 3100 can be used as a stand in order to hold the delivery system 12 at a particular position. However, in some embodiments the legs 3100 can be removed in order to directly connect the joint 3200 to another device such as, for example, a robotic arm through the mating components discussed above.

These legs 3100 can be attached to the joint 3200 so that they can articulate with respect to the joint 3200, allowing for the changing of position of the legs 3100, and thus the overall position of the delivery system 12. In some embodiments, the adapter 3000 can include a locking mechanism to prevent motion of the legs 3100. In some embodiments, a significant force is needed to move the legs 3100 so that they do not accidentally move during operation, and thus a locking mechanism may not be used.

The joint 3200 can be attached to a delivery system attachment mechanism 3400 in a similar fashion as discussed above with respect to the previous ball in socket adapter 2000. As shown, the adapter 3000 can include a ball 3402 located within a cavity 3406 in the joint 3200. The ball 3402 can be attached to a member 3404 extending out of an aperture 3408 in the joint 3200 from the cavity 3406 and attached to the delivery system attachment mechanism 3400. Accordingly, the ball 3402 can rotate within the cavity 3406 to provide three dimensional motion of the delivery system attachment mechanism 3400, and is only constrained by the size of the aperture 3408.

While not shown, the delivery system attachment mechanism can include components discussed above, such as the linear guide element 2200 and clamp 2100 to attach the adapter 3000 to a delivery system 12.

In some embodiments, the joint can include a locking mechanism 3500, as shown in FIG. 19. The locking mechanism 3500 can be a rotatable knob or push-button, though the particular mechanism is not limiting. For example, a push button can be used to engage and disengage a lock so that the ball 3402 is locked in place within the joint 3402 can be locked in place within the joint. The type of locking mechanism is not limiting and the discussed locking mechanisms can be used interchangeably between the different ball and socket adapters.

From the foregoing description, it will be appreciated that an inventive product and approaches for implant delivery systems are disclosed. While several components, techniques and aspects have been described with a certain degree of particularity, it is manifest that many changes can be made in the specific designs, constructions and methodology herein above described without departing from the spirit and scope of this disclosure.

Certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as any subcombination or variation of any subcombination.

Moreover, while methods may be depicted in the drawings or described in the specification in a particular order, such methods need not be performed in the particular order shown or in sequential order, and that all methods need not be performed, to achieve desirable results. Other methods that are not depicted or described can be incorporated in the example methods and processes. For example, one or more additional methods can be performed before, after, simultaneously, or between any of the described methods. Further, the methods may be rearranged or reordered in other implementations. Also, the separation of various system components in the implementations described above should not be understood as requiring such separation in all implementations, and it should be understood that the described components and systems can generally be integrated together in a single product or packaged into multiple products. Additionally, other implementations are within the scope of this disclosure.

Conditional language, such as "can," "could," "might," or "may," unless specifically stated otherwise, or otherwise understood within the context as used, is generally intended to convey that certain embodiments include or do not include, certain features, elements, and/or steps. Thus, such conditional language is not generally intended to imply that features, elements, and/or steps are in any way required for one or more embodiments.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than or equal to 10% of, within less than or equal to 5% of, within less than or equal to 1% of, within less than or equal to 0.1% of, and within less than or equal to 0.01% of the stated amount. If the stated amount is 0 (e.g., none, having no), the above recited ranges can be specific ranges, and not within a particular % of the value. For example, within less than or equal to 10 wt./vol. % of, within less than or equal to 5 wt./vol. % of, within less than or equal to 1 wt./vol. % of, within less than or equal to 0.1 wt./vol. % of, and within less than or equal to 0.01 wt./vol. % of the stated amount.

Some embodiments have been described in connection with the accompanying drawings. The figures are drawn to scale, but such scale should not be limiting, since dimensions and proportions other than what are shown are contemplated and are within the scope of the disclosed inventions. Distances, angles, etc. are merely illustrative and do not necessarily bear an exact relationship to actual dimensions and layout of the devices illustrated. Components can be added, removed, and/or rearranged. Further, the disclosure herein of any particular feature, aspect, method, property, characteristic, quality, attribute, element, or the like in connection with various embodiments can be used in all other embodiments set forth herein. Additionally, it will be recognized that any methods described herein may be practiced using any device suitable for performing the recited steps.

While a number of embodiments and variations thereof have been described in detail, other modifications and methods of using the same will be apparent to those of skill in the art. Accordingly, it should be understood that various applications, modifications, materials, and substitutions can be made of equivalents without departing from the unique and inventive disclosure herein or the scope of the claims.

What is claimed is:

1. A system for facilitating controllable delivery of a replacement heart valve, the system comprising:
    a replacement heart valve;
    a replacement heart valve delivery device configured to controllably deliver the replacement heart valve within a heart of a subject, the delivery device comprising a handle;
    a steerable adapter configured to manipulate a position of the handle of the delivery device, the steerable adapter comprising:
        a clamp configured to receive and retain the handle of the delivery device, the clamp comprising an upper arm and a lower arm, wherein the upper arm and the lower arm each comprise a generally c-shaped section and a linear section, wherein the generally c-shaped section of the upper arm and the generally c-shaped section of the lower arm are configured to face one another;
        a screw configured to pass through the linear sections of the upper arm and the lower arm;
        a knob attached to the screw configured to tighten or loosen the clamp;
        a stopper located on the screw between the linear sections of the upper arm and the lower arm configured to prevent the knob from falling off the clamp after the screw has completely disengaged from the lower arm;
        a u-shaped bracket having a first leg comprising a first end and a second end, a second leg comprising a first end and a second end, the second leg spaced apart from the first leg, and a connector leg connecting the first end of the first leg and the first end of the second leg, the second end of the first leg and the second end of the second leg being free ends, the first leg, the second leg, and the connector leg being unitary, wherein a portion of the clamp extends between the first leg and the second leg opposite of the connector leg and interfaces with a linear screw extending between the first leg and the second leg configured to translate the clamp along the linear screw, the u-shaped bracket having at least one knob configured to translate the clamp along the linear screw extending between the first leg and the second leg;
        a guide block spanning between inside surfaces of the second leg and the first leg and running generally parallel to the connector leg;
        a T-shaped connector block located between the first leg and the second leg, the T-shaped connector block threadedly attached to the linear screw through a threaded aperture in the T-shaped connector block, wherein the T-shaped connector block further includes another aperture configured to slidably receive the guide block, wherein the T-shaped connector block is connected to the clamp;
        a first gear directly attached to the u-shaped bracket and configured to be rotated;
        a first support platform rotatably attached to the first gear;
        a second gear directly fixedly attached to the first support platform and configured to be rotated;
        a second support platform rotatably attached to the second gear; and a mating component located on the second support platform, the mating component configured to connect to an outside component.

2. The system of claim 1, wherein each of the first and second support platforms are generally L-shaped.

3. The system of claim 1, wherein the clamp is configured to translate and/or rotate in three dimensions.

4. The system of claim 1, wherein the first gear is configured to rotate the clamp on a plane perpendicular to the plane created by rotation of the second gear.

5. The system of claim 1, wherein the mating component is configured to releasably mate with the outside component.

6. The system of claim 1, wherein the first leg, the second leg, and the connector leg are generally rectangular in shape.

7. A system for facilitating controllable delivery of a replacement heart valve, the system comprising:
    a replacement heart valve;
    a replacement heart valve delivery device configured to controllably deliver the replacement heart valve within a heart of a subject, the delivery device comprising a handle;
    a steerable adapter configured to manipulate a position of the handle of the delivery device, the steerable adapter comprising:
        a clamp configured to hold the handle of the delivery device;
        a first knob configured to provide translational motion of the clamp along a longitudinal axis of the handle of the delivery device;
        a second knob configured to provide rotational motion of the clamp along a first rotational axis;
        a third knob configured to provide rotational motion of the clamp along a second rotational axis;
        an h-shaped member translatably attached to the clamp, the h-shaped member including a long leg opposite a short leg, with a connector leg connecting an end of the short leg and a midsection of the long leg;
        a guide block spanning between inside surfaces of the short leg and the long leg and running generally parallel to the connector leg;
        a pair of U-shaped members, each U-shaped member attached to one of the second or third knobs, wherein the U-shaped members are configured to rotate with respect to one another to provide the rotational motion to the clamp; and
        an x-shaped member formed from a first leg connected generally at a center to a second leg forming an x-shape, wherein the first leg extends between and connects opposite legs of a first U-shaped member of the pair of U-shaped members and the second leg extends between and connects opposite legs of a second U-shaped member of the pair of U-shaped members, the x-shaped member acting as a rotation axis for rotation of the first U-shaped member with respect to the second U-shaped member,
        wherein the first rotational axis is generally perpendicular to the second rotational axis.

8. The system of claim 7, further comprising a mating component configured to releasably mate with a component outside of the steerable adapter.

9. The system of claim 7, wherein the clamp is configured to translate or rotate in three dimensions.

10. The system of claim 7, further comprising a T-shaped connector block located between the long leg and the short leg of the h-shaped member, wherein the T-shaped connector block includes an aperture configured to slidably receive the guide block therein.

11. A system for facilitating controllable delivery of a replacement heart valve, the system comprising:
    a replacement heart valve;
    a replacement heart valve delivery device configured to controllably deliver the replacement heart valve within a body of a subject, the delivery device comprising a handle;
    a steerable adapter configured to manipulate a position of the handle of the delivery device, the steerable adapter comprising:
        a clamp configured to receive and retain the handle;
        a bracket having a first leg comprising a first end and a second end, a second leg comprising a first end and a second end, the second leg spaced apart from the first leg by a connector leg connected to the first end of the first leg and the first end of the second leg to form a U-shaped structure, the first leg, the second leg, and the connector leg being unitary, wherein a portion of the clamp extends within a gap between the first leg and the second leg and interfaces with a linear screw extending between the first leg and the second leg configured to translate the clamp along the linear screw, the bracket having at least one actuator configured to translate the clamp along the linear screw extending between the first leg and the second leg;
        a first gear directly attached to the bracket and configured to be rotated;
        a first support platform rotatably attached to the first gear;
        a second gear directly fixedly attached to the first support platform and configured to be rotated; and
        a second support platform rotatably attached to the second gear.

12. The system of claim 11, wherein the steerable adapter further comprises a mating component configured to releasably mate with a component outside of the steerable adapter.

13. The system of claim 11, wherein the first leg, the second leg, and the connector leg are generally rectangular in shape.

14. The system of claim 11, wherein the at least one actuator comprises a knob.

15. The system of claim 11, wherein the steerable adapter further comprises a plurality of knobs configured to rotate the first gear and the second gear.

16. The system of claim 11, further comprising a guide block spanning between inside surfaces of the second leg and the first leg and running generally parallel to the connector leg.

17. The system of claim 11, further comprising a T-shaped connector block located between the first leg and the second leg, the T-shaped connector block threadedly attached to the linear screw through a threaded aperture in the T-shaped connector block.

18. The system of claim 11, wherein the T-shaped connector block is connected to the clamp.

* * * * *